(12) United States Patent
Shizuru et al.

(10) Patent No.: US 12,233,093 B2
(45) Date of Patent: *Feb. 25, 2025

(54) ENGRAFTMENT OF STEM CELLS WITH A COMBINATION OF AN AGENT THAT TARGETS STEM CELLS AND MODULATION OF IMMUNOREGULATORY SIGNALING

(71) Applicant: The Board of Trustees of the Leland Stanford Junior University, Stanford, CA (US)

(72) Inventors: Judith A. Shizuru, Palo Alto, CA (US); Irving L. Weissman, Stanford, CA (US); Kipp Andrew Weiskopf, Sudbury, MA (US); Aaron Michael Ring, New Haven, CT (US); Akanksha Chhabra, San Francisco, CA (US); Peter Schnorr, Sudbury, MA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 259 days.

This patent is subject to a terminal disclaimer.

(21) Appl. No.: 17/867,321

(22) Filed: Jul. 18, 2022

(65) Prior Publication Data

US 2022/0347224 A1 Nov. 3, 2022

Related U.S. Application Data

(63) Continuation of application No. 16/526,794, filed on Jul. 30, 2019, now Pat. No. 11,419,897, which is a continuation of application No. 15/504,264, filed as application No. PCT/US2015/046976 on Aug. 26, 2015, now Pat. No. 10,406,179.

(60) Provisional application No. 62/041,989, filed on Aug. 26, 2014.

(51) Int. Cl.
| | |
|---|---|
| *A61K 35/28* | (2015.01) |
| *A61K 38/17* | (2006.01) |
| *A61K 39/00* | (2006.01) |
| *A61K 39/395* | (2006.01) |
| *A61K 45/06* | (2006.01) |
| *C07K 16/28* | (2006.01) |

(52) U.S. Cl.
CPC .......... *A61K 35/28* (2013.01); *A61K 38/1709* (2013.01); *A61K 38/1774* (2013.01); *A61K 38/1793* (2013.01); *A61K 39/3955* (2013.01); *A61K 45/06* (2013.01); *C07K 16/2803* (2013.01); *C07K 16/2878* (2013.01); *C07K 16/2896* (2013.01); *A61K 2039/505* (2013.01); *A61K 2039/507* (2013.01); *C07K 2317/74* (2013.01); *C07K 2317/75* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,686,278 | A | 11/1997 | Williams et al. |
| 10,105,451 | B2 | 10/2018 | Leboulch et al. |
| 2009/0191202 | A1 | 7/2009 | Jamieson et al. |
| 2010/0226927 | A1 | 9/2010 | Weissman et al. |
| 2010/0239579 | A1 | 9/2010 | Smith et al. |

FOREIGN PATENT DOCUMENTS

| | | |
|---|---|---|
| WO | WO2004002425 | 1/2004 |
| WO | WO2008067115 | 6/2008 |
| WO | WO2009091601 | 7/2009 |
| WO | WO2011/034969 | 3/2011 |
| WO | WO2013/056352 | 4/2013 |
| WO | WO2013/109752 | 7/2013 |
| WO | WO 2015138600 | 9/2015 |
| WO | WO2016033201 | 3/2016 |
| WO | WO2016205042 | 12/2016 |

OTHER PUBLICATIONS (2006) Chapter 2 of Regenerative Medicine, Department of Health and Human Services.
Ballas, (2002). "Sickle cell anaemia: progress in pathogenesis and treatment", Drugs. 62(8):1143-72.
Bartkowiak & Curran, (2015). "4-1BB Agonists: Multi-Potent Potentiators of Tumor Immunity", Front Oncol. 5:117.
Chhabra et al., (2014) "Successful Engraftment of Hematopoietic Stem Cells into Immunocompetent Recipients Using Only Anti-CD117 Antibody and CD47 Blockade As Conditioning.", Blood. 124(21):241.
Chhabra et al., (2016) "Hematopoietic stem cell transplantation in immunocompetent hosts without radiation or chemotherapy", Science Translation Medicine, pp. 1-10, vol. 8 No. 351, American Association for the Advancement of Science, Washington, DC.

(Continued)

Primary Examiner — Daniel C Gamett
(74) Attorney, Agent, or Firm — Pamela J. Sherwood; Bozicevic, Field & Francis LLP

(57) ABSTRACT

The present invention provides a clinically applicable method of stem cell transplantation that facilitates engraftment and reconstitutes immunocompetence of the recipient without requiring radiotherapy or chemotherapy, and without development of GVHD or graft rejection. Aspects of the present invention are based on the discovery that the depletion of the endogenous stem cell niche facilitates efficient engraftment of stem cells into that niche. In particular, the present invention combines the use of selective ablation of endogenous stem cells with a combination of antibodies specific for CD117, and agents that modulate immunoregulatory signaling pathways, e.g. agonists of immune costimulatory molecules, in combination with the administration to the recipient of exogenous stem cells, resulting in efficient, long-term engraftment, even in immunocompetent recipients.

17 Claims, 21 Drawing Sheets

(56) References Cited

OTHER PUBLICATIONS

Edris et al., (2013). "Use of a KIT-specific monoclonal antibody to bypass imatinib resistance in gastrointestinal stromal tumors", Oncoimmunology, 2(6): e24452.
Farmakis et al., (2003). "Pathogenetic aspects of immune deficiency associated with beta-thalassemia", Med Sci Monit. 9(1):RA19-22.
Grez et al., (2011). "Gene therapy of chronic granulomatous disease: the engraftment dilemma", Mol Ther. 19(1):28-35.
Henig & Zuckerman, (2014)., "Hematopoietic stem cell transplantation—50 years of evolution and future perspectives" Rambam Maimonides Med J. 5(4): e0028.
Kohn et al., (2013). "Gene therapy through autologous transplantation of gene-modified hematopoietic stem cells" Bioi Blood Marrow Transplant. 19(1 Suppi):S64-9.
Kontermann, (2012). "Dual targeting strategies with bispecific antibodies", MAbs. 4(2): 182-97.
Larochelle & Dunbar, (2013). "Hematopoietic stem cell gene therapy: assessing the relevance of preclinical models", Semin Hematol. 50(2):101-30 (available in PMC Apr. 1, 2014).
Lennartsson & Ronnstrand, (2012). "Stem cell factor receptor/c-Kit: from basic science to clinical implications", Phsyiol Rev. 92(4):1619-49.
Logan et al., (2012). "The road to purified hematopoietic stem cell transplants is paved with antibodies", Curr Opin Immunol. 24(5): 640-648.
Murata et al., (2014). "The CD47-SIRPα signaling system: its physiological roles and therapeutic application", J Biochem. 155(6):355-44.
Nickel et al. (2014) The ethics of a proposed study if hem Hematopoietic Stem Cell Transplantation for Children with "less severe" sickle cell disease. Blood, 124;(6) pp. 861-866.
Pai et al. (2014) Transplantation outcomes for severe Combined Immunodeficiency, 2000-2009, 31; 371(5) pp. 434-446.
Pang (2019) "Anti-human CD117 antibody-mediated bone marrow niche clearance in nonhuman primates and humanized NSG mice" Blood 133(19).
Peinemann & Labeit, (2014). "Autologous hematopoietic stem cell transplantation following high-dose chemotherapy for non-rhabdomyosarcoma soft tissue sarcomas: a Cochrane systematic review", BMJ Open, 4(7): e005033.
Petersen, (2007). "Alloreactivity as therapeutic principle in the treatment of hematologic malignancies. Studies of clinical and immunologic aspects of allogeneic hematopoietic cell transplantation with nonmyeloablative conditioning", Dan Med Bull. 54(2): 112-39.
Raut et al. (2015) Improving Outcome of Aplastic with HLA-Matched Sibling Donor Hematopoietic Stem Cell Transplantation: An Experience of Gurat Cancer and Research Institute, 31(1); pp. 1-8.
Rozanov et al., (2015). "A humanized leucine zipper-TRAIL hybrid induces apoptosis of tumors both in vitro and in vivo", PLoS One. 10(4): e0122980.
Schroeder & Cavacini, (2010), "Structure and function of immunoglobulins", J Allergy Clin Immunol. 125(2): S41-S52.
Tavare (2014), "Engineered antibody fragments for immuno-PET imaging of endogenous CD8+ T cells in vivo", PNAS 111(3): 1108-1113.
Valdez et al., (2009) "Infections in patients with aplastic anemia", Semin Hematol. 46(3):269-76.
Viola-Villegas (2014), "Noninvasive Imaging of PSMA in prostate tumors with (89)Zr-Labeled huJ591 engineered antibody fragments: the faster alternatives", Molecular Pharmaceutics 11:3965 3973.
Weiskopf & Weissman, (2015). "Macrophages are critical effectors of antibody therapies for cancer", MAbs. 7(2): 303-310.
Weiskopf et al., "Improving macrophage responses to therapeutic antibodies by molecular engineering of SIRP α variants" OncoImmunology, Sep. 2013, pp. e25773-1-e25773-3, vol. 2, No. 9, Landes Bioscience, Austin, TX.
Weiskopf et al., (2016)., "Myeloid Cell Origins, Differentiation, and Clinical Implications", Microbiol Spectr.4(5): 10.1128/microbiolspec. MCHD-0031-2016.
Xue et al., (2010) "Antibody targeting KIT as pre-transplantation conditioning in immunocompetent mice" Blood. 116(24):5419-22.
Chhabra et al. (2014) "Successful Engraftment of Hematopoietic Stem Cells into Immunocompetent Recipients Using Only Anti-CD117 Antibody and CD47 Blockade As Conditioning." *Blood*, 124(21) p. 2410.
Petersen (2007) "Alloreactivity as therapeutic principle in the treatment of hematologic malignancies." *Dan Med Bull*, 54(2), pp. 112-139.
Schroeder et al. (2010) "Structure and function of immunoglobulins." *Journal of allergy and clinical immunology*, 125(2), pp. S41-S52.
Grounds for the interlocutory decision in the Jan. 21, 2020, Opposition proceedings of EP 07871350.0.
Patentee's submission of Feb. 21, 2018 in the prosecution of EP 15762121.0.

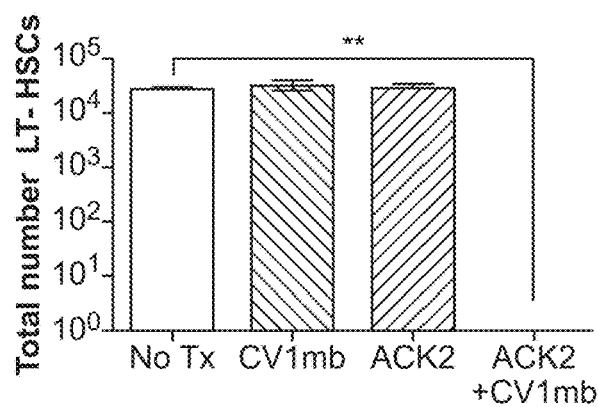
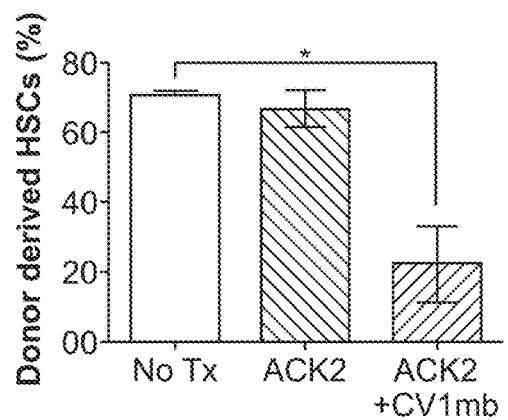
FIG. 4a  FIG. 4b
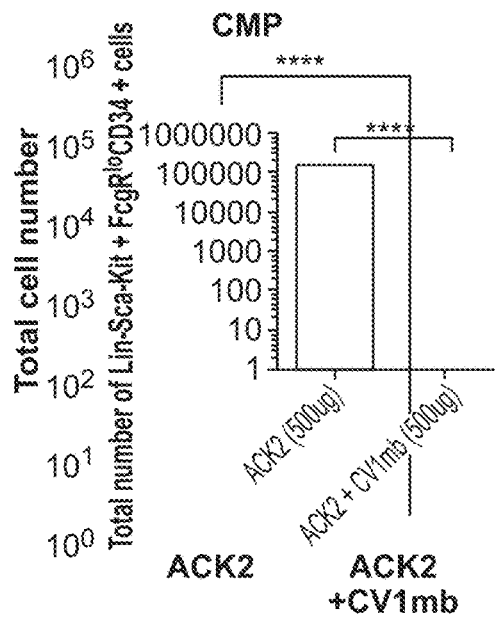
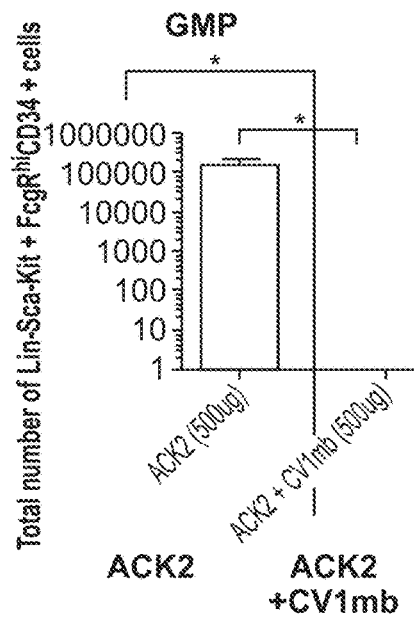
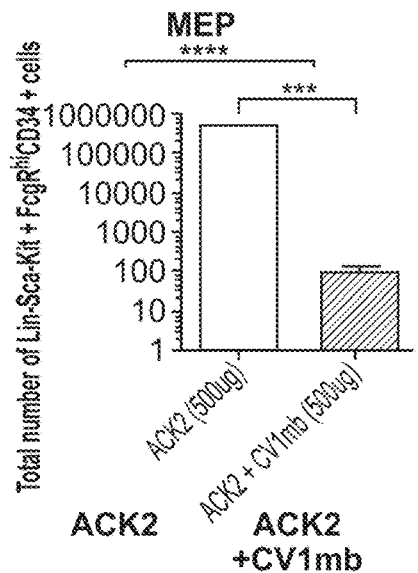
FIG. 4c

Allogeneic HSC transplant
(mHC mismatch- ACK2 + CV1mb conditioning)

Allogeneic HSC transplant (mHC mismatch, Wk 4)

Allogeneic HSC transplant (Haplo-identical, Wk 4)

Donor Granulocyte Chimerism

Donor B-Cell Chimerism

Allogeneic HSC transplant (MHC mismatch, Wk 4)

Donor Granulocyte Chimerism

+ anti-CD4 and anti-CD8

Donor B-Cell Chimerism

+ anti-CD4 and anti-CD8

ENGRAFTMENT OF STEM CELLS WITH A COMBINATION OF AN AGENT THAT TARGETS STEM CELLS AND MODULATION OF IMMUNOREGULATORY SIGNALING

CROSS REFERENCE

This application is a continuation application and claims benefit of U.S. application Ser. No. 16/526,794, filed Jul. 30, 2019, which claims the benefit of 371 application Ser. No. 15/504,264, filed Feb. 15, 2017, now U.S. Pat. No. 10,406, 179, issued Sep. 10, 2019, which claims benefit of PCT Application No. PCT/US2015/046976, filed Aug. 26, 2015, which claims benefit of U.S. Provisional Patent Application No. 62/041,989, filed Aug. 26, 2014, which applications are incorporated herein by reference in their entirety.

Stem cells provide the means for organisms to maintain and repair certain tissues, through the ability of these cells to self-renew and to generate differentiated cells. Clinically, bone marrow and hematopoietic stem cell transplantation are widely used as a means of providing patients with the capacity to generate blood cells, usually where the patient has been depleted of endogenous stem cells by high dose chemotherapy or radiation.

Hematopoietic cell transplantation (HCT) generally involves the intravenous infusion of autologous or allogeneic blood forming cells, the active subset of which are hematopoietic stem cells [HSC]; these are collected from bone marrow, peripheral blood, or umbilical cord blood and transplanted to reestablish hematopoietic function in patients whose bone marrow or immune system is damaged or defective. This procedure is often performed as part of therapy to eliminate a bone marrow infiltrative process, such as leukemia, or to correct congenital immunodeficiency disorders. In addition, HCT is used to allow patients with cancer to receive higher doses of chemotherapy than bone marrow can usually tolerate; bone marrow function is then salvaged by replacing the marrow with previously harvested stem cells. Enriched or purified populations of HSC can also be transplanted, and are not contaminated with other cells, many of which are deleterious to the host.

The list of diseases for which HSCT is being used is rapidly increasing. More than half of the autologous transplantations are performed for multiple myeloma and non-Hodgkin lymphoma and a vast majority of allogeneic transplants are performed for hematologic and lymphoid cancers.

The preparative or conditioning regimen is a critical element in hematopoietic cell transplantation (HCT). In a successful transplantation, clearance of bone-marrow niches must be achieved for donor hematopoietic stem cell (HSC) to engraft. The preparative regimen may also provide immunosuppression sufficient to prevent rejection of the transplanted graft, and to eradicate the disease for which the transplantation is being performed. Current methods to clear niche space rely on radiation and/or chemotherapy, which can impart toxic adverse effects that greatly limit the potential clinical utility of BMT. Traditionally, myeloablative conditioning is performed.

Myeloablative regimens can be classified as radiation-containing or non-radiation-containing regimens, therapies that were developed by escalating the dose of radiation or of a particular drug to the maximally tolerated dose. Total-body irradiation and cyclophosphamide or busulfan and cyclophosphamide are the commonly used myeloablative therapies. These regimens are especially used in aggressive malignancies, such as leukemias. However, such treatment carries a number of disadvantages in terms of toxicity to the patient.

Improved methods for engraftment of stem cells, including hematopoietic stem cells, are of great clinical interest. The present invention addresses this need.

SUMMARY OF THE INVENTION

Methods are provided for engraftment of stem cells, including without limitation hematopoietic stem cells, in a recipient with a pre-transplantation conditioning regimen comprising an agent that targets stem cells, including without limitation an antibody specific for CD117; and agent(s) that modulate immunoregulatory signaling. Immunoregulatory modulating agents may comprise one or both of (i) an agent that blockades CD47 activity; and (ii) an agent that agonizes an immune costimulatory molecule, e.g. CD137. An agonist of CD137, when present, can be administered prior to CD47 blockade, after CD47 blockade, or concomitantly with CD47 blockade. In some embodiments, the transplantation is performed in the absence of myeloablative conditioning. In some embodiments the recipient is immunocompetent. The administration of the pre-transplantation conditioning regimen is repeated as necessary to achieve the desired level of ablation.

In some embodiments the CD47 blockade is accomplished by administering a soluble SIRPα polypeptide, which may be a high affinity SIRPα variant polypeptide. In other embodiments, antibodies specific for one or both of SIRPα and CD47 are administered. Optionally the method includes administering an agonist of a costimulatory molecule, for example a CD137 agonist, which can include, without limitation, the native ligand (TNFSF9), aptamers, and antibodies.

Following transplantation with donor stem cells, the recipient may be a chimera or mixed chimera for the donor cells. The methods of the invention allow effective stem cell engraftment in the absence of non-selective ablation methods, e.g. radiation or chemotherapy, which have the undesirable effect of ablating differentiated cells involved in the function of the targeted tissue as well as undesirable side effects upon other tissues (e.g. on cells of the gastrointestinal system, hair growth), as well as increasing risk of secondary malignancies.

In one embodiment of the invention, the stem cells are one or more of autologous hematopoietic stem cells, genetically modified hematopoietic stem cells, and allogeneic hematopoietic stem cells. Such stem cells find use in the treatment of a variety of blood disorders, e.g. genetic disorders including aplastic anemia; sickle cell disease; thalassemias; severe immunodeficiency; bone marrow failure states, immune deficiencies, hemoglobinopathies, leukemias, lymphomas, immune-tolerance induction, genetic disorders treatable by bone marrow transplantation and other blood disorders, and the like.

The methods of the invention are also useful in the induction of tolerance in a patient, for example tolerance to donor tissue, e.g. in organ transplants; tolerance to autoantigens, e.g. in the context of treatment of autoimmune disease; and the like. In one embodiment of the invention, a method is provided for inducing tolerance in a patient, comprising administering to a patient a therapeutically effective combined dose of antibodies to a stem cell marker, and an agent that provides for CD47 blockade. Optionally an agonist of a costimulatory molecule, e.g. CD137, is also included. This conditioning regimen can be combined with lymphoid cell depleting antibodies and agents that target T cells, B cells and NK cells such as but not limited to anti-CD4, anti-CD8, anti-NK and anti-B220 to facilitate allogeneic HSC transplantation as demonstrated by our studies below.

BRIEF DESCRIPTION OF THE FIGURES

(FIG. 2a), Total number of phenotypic lineage-c-Kit+Sca-1+CD150+Flt3-CD34− long-term HSCs in wild type (WT) mice as compared to immunocompromised Rag2−/−cγ−/− mice post-treatment with anti c-Kit antibody ACK2 (n=3-5). (FIG. 2b), Total frequency of lineage-c-Kit+Sca-1+CD150+Flt3-CD34− long-term HSCs in Rag2−/−cγ−/− mice six days after treatment with increasing concentrations of ACK2 compared to 500 µg of ACK2 Fab. (n=3) (c), Number of lineage-c-Kit+Sca-1+CD150+Flt3− CD34− long-term HSCs in FcR−/− mice six days post-ACK2 treatment as compared to untreated controls (n=3, experiment was replicated in triplicate). (d), Frequency of donor-derived lineage-c-Kit+ Sca-1+ HSCs present 18 weeks after transplant into irradiated recipients. Recipients were transplanted with 1,000,000 donor whole bone marrow cells and 1,000,000 support GFP+ cells (n=3, experiment was replicated in duplicate). Data and error bars in panels b, c, and d represent the mean±s.e.m. NS, not significant; ** p<0.0001, * p<0.0005, ** p<0.005.

(FIG. 3a), Schematic of CV1 and CV1mb. CV1mb is a fusion of CV1 to the dimeric CH3 domain of human IgG1 linked by a disulfide-containing hinge. (FIG. 3b), Phagocytosis of EGFR+ DLD1 colon cancer cells by human macrophages after treatment with cetuximab (anti-EGFR) with and without CV1 and CV1mb, as indicated as a percentage of maximal response.

FIG. 4a-4e. Anti-c-Kit antibody combined with CD47 blockade with CV1mb produces profound depletion of HSCs in immunocompetent mice and clearance of the bone marrow niche. (FIG. 4a), Total number of lineage-c-Kit+ Sca-1+CD150+Flt3−CD34− long-term HSCs in wild-type (WT) mice post 7 days of treatment with anti-c-Kit antibody ACK2, CD47 antagonist CV1mb and combination of ACK2 and CV1mb as compared to untreated controls (n=3, experiment was replicated 4 times). (FIG. 4b), Frequency of donor derived HSCs in the bone marrow present 24 weeks after transplant into irradiated recipients. Recipients were transplanted with 1,000,000 donor whole bone marrow cells and 1,000,000 support GFP+ bone marrow cells (n=5). (FIG. 4c), Total number of downstream myeloid progenitors are decreased post 7 days of treatment with ACK2 and CV1mb as compared to ACK2 alone. CMP, common myeloid progenitor (Lin−Sca-1+c-Kit+FcRgloCD34+); GMP, granulocyte macrophage progenitor (Lin−Sca-1−c-Kit+FcRghiCD34+); MEP, megakaryocyte erythroid progenitor (Lin−Sca-1−c-Kit+FcRgloCD34−). (FIG. 4d), Complete blood counts of peripheral blood of WT mice 7 days after treatment with anti-c-Kit antibody ACK2, CD47 antagonist CV1mb and combination of ACK2 and CV1mb as compared to untreated controls (n=3, experiment was replicated in triplicate). (FIG. 4e), Hematoxylin and eosin staining of bone marrow section depicting loss of bone marrow cellularity at 7 days in ACK2 and CV1mb treated mice as compared to mice treated with ACK2 alone. Data and error bars in panels b, c, and d represent the mean±s.e.m. NS, not significant; ** p<0.0001, * p<0.005, ** p<0.01, * p<0.05.

(FIG. 5a), Schematic of protocol for conditioning of recipients with anti-c-Kit antibody ACK2 and CD47 antagonist CV1mb. F1 mice expressing both alleles CD45.1 and CD45.2 were treated with 500 µg of ACK2 once and 500 µg of CV1mb daily for 5 days. On the sixth day post-treatment, 1,000,000 CD45.2+donor lineage-cells were transplanted daily for 3 days. Severely anemic mice were administered blood transfusions (n=3-5, experiment was replicated in triplicate). (FIG. 5b), Frequency of donor derived lineage-c-Kit+Sca-1+CD150+ HSCs in the bone marrow 24 weeks after transplant in ACK2 and CV1mb treated recipients as compared to mice treated with ACK2 alone (n=3-5, experiment was replicated in triplicate). (FIG. 5c), Donor chimerism of Gr-1+Mac-1+ granulocytes. (FIG. 5d), Donor derived chimerism of CD19+ B cells. (FIG. 5e), Donor derived chimerism of NK1.1+ natural killer cells. (FIG. 5f), Donor derived chimerism of CD3+ T cells. All analyses were performed for peripheral blood 20 weeks after transplant in ACK2 and CV1mb treated recipients as compared to mice treated with ACK2 alone (n=3-5, experiment was replicated in triplicate). Data and error bars in panels b-f represent the mean±s.e.m. ** p<0.0001, * p<0.005

(FIG. 6b), Donor derived chimerism of CD19+ B cells in bone marrow. Donor derived chimerism of NK1.1+ natural killer cells in (FIG. 6c), bone marrow and (FIG. 6g), spleen. (FIG. 6d), Donor derived chimerism of CD3+ T cells in the bone marrow. (FIG. 6f), Donor derived CD19+B220+ B cells and (FIG. 6h), CD3+ TCRβ+ T cells in spleen. (FIG. 6i), CD4+ Thy1.1+ T cell chimerism in the thymus. Data and error bars in panels represent the mean±s.e.m. ** p<0.0001, * p<0.005.

(FIG. 7b), Frequency of donor derived Mac1+Gr-1+ granulocytes in the peripheral blood 8 weeks post transplant into irradiated recipients. Recipients were transplanted with 1,000,000 treated donor whole bone marrow cells and 1,000,000 support bone marrow cells. b represent the mean±s.e.m. * p<0.05, n=3-6).

(FIG. 9a), LSK HSCs were sorted from B10.D2 Donors and transplanted as per our conditioning regiment into anti-c-Kit and anti-CD47 treated Balb/C mice. Granulocyte chimerism was determined by FACS analysis of Mac-1+Gr-1+ cells. (FIG. 9b), LSK HSCs were sorted from B10.D2 Donors and transplanted as per our conditioning regiment into anti-c-Kit and anti-CD47 treated Balb/C mice. B-cell chimerism was determined by FACS analysis of CD19+ cells. (FIG. 9c), LSK HSCs were sorted from B10.D2 Donors and transplanted as per our conditioning regiment into anti-c-Kit and anti-CD47 treated Balb/C mice. B-cell chimerism was determined by FACS analysis of CD3+ cells. Stable multi-lineage (myeloid and lymphoid) chimerism was observed.

(FIG. 11a), BA (CD45.2) Granulocyte Chimerism in Treated F1 (CD45.2×CD45.1) animals at four weeks post transplant. F1 mice (CD45.2×CD45.1) received the indicated antibody regimens and then received three lineage negative transplants. Donor granulocyte chimerism was measured four weeks post transplant via fluorescence-activated cell sorting. The triple therapy (anti-CD137+anti-CD47 (MIAP410)+anti-CD117) treated mice had a greater than four-fold increase in donor granulocyte chimerism than the mice treated with anti-CD47+anti-CD117 alone (p value<0.0001). Anti-CD137 greatly increases the efficacy of anti-CD47 in the transplant setting. (FIG. 11b), BA (CD45.2) B-Cell Chimerism in Treated F1 (CD45.2× CD45.1) animals at four weeks post transplant. F1 mice (CD45.2×CD45.1) received the indicated antibody regimens and then received three lineage negative transplants. Donor B-cell chimerism was measured four weeks post transplant via fluorescence-activated cell sorting. The triple therapy (anti-CD137+anti-CD47+anti-CD117) treated mice had a greater than eight-fold increase in donor B-cell chimerism than the mice treated with anti-CD47+anti-CD117 alone (p value=0.0028). Anti-CD137 greatly increases the efficacy of anti-CD47 antibody in the transplant setting.

(FIG. 12a), Granulocyte chimerism was determined by FACS analysis of Mac-1+Gr-1+ cells. (FIG. 12b), B-cell chimerism was determined by FACS analysis of CD19+ cells. Multi-lineage chimerism (myeloid and lymphoid) was observed.

(FIG. 13a), Granulocyte chimerism was determined by FACS analysis of Mac-1+Gr-1+ cells. (FIG. 13b), B-cell chimerism was determined by FACS analysis of CD19+ cells. Multi-lineage chimerism (myeloid and lymphoid) was observed.

(FIG. 14a), Granulocyte chimerism was determined by FACS analysis of Mac-1+Gr-1+ cells. (FIG. 14b), B-cell chimerism was determined by FACS analysis of CD19+ cells. Multi-lineage chimerism (myeloid and lymphoid) was observed.

DETAILED DESCRIPTION OF THE EMBODIMENTS

Figure 1:
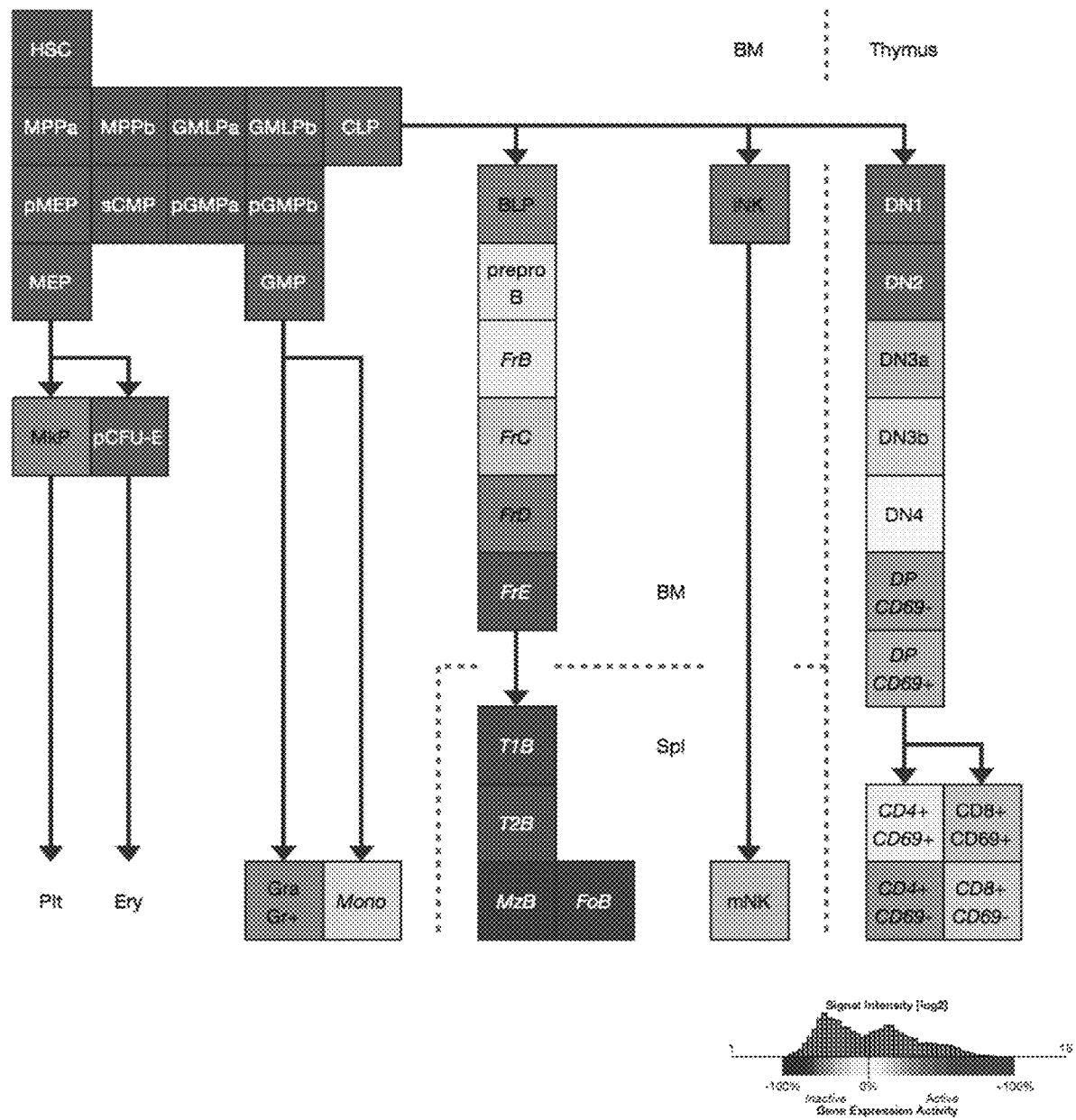
FIG. 1. Expression of c-Kit during hematopoiesis. Summary of c-Kit expression in hematopoietic stem and progenitor cells and differentiated cells in major hematopoietic organs from Gene Expression Commons.
Figure 2A:
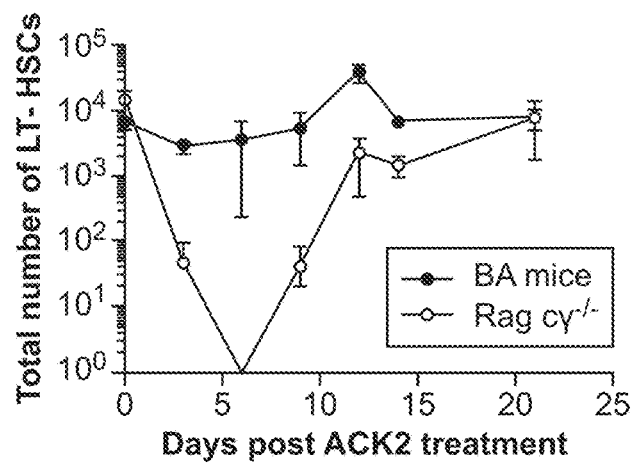
FIG. 2a-2d. Depletion of HSCs by anti-c-Kit antibody ACK2 is dependent on Fc receptor activity.
Figure 2B:
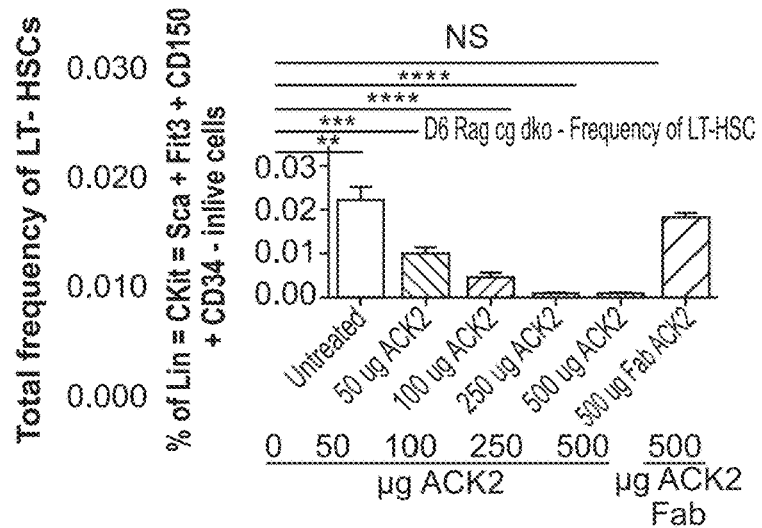
Figure 2C:
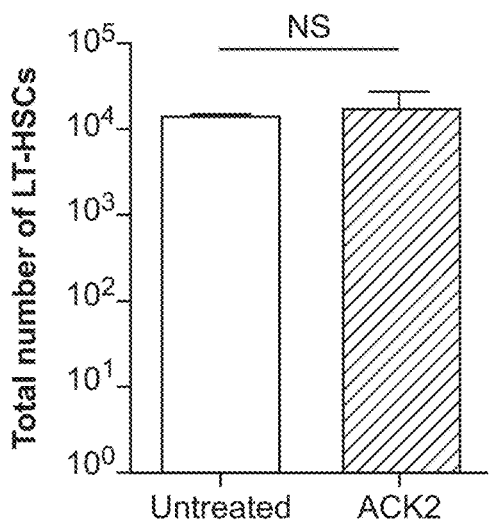
Figure 2D:
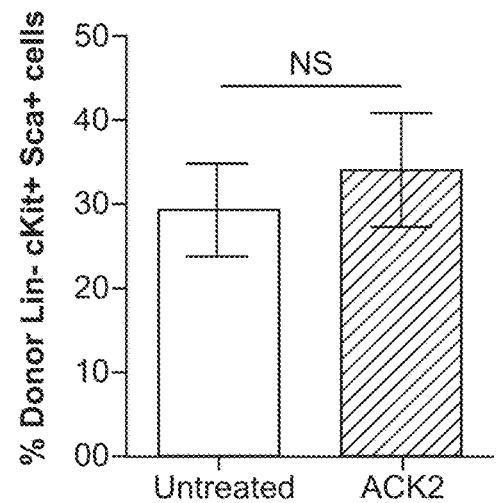

Methods are provided for the engraftment of stem cells in a subject, where endogenous stem cells are selectively ablated by a combined therapy of an agent, e.g. antibodies, that selectively bind to a stem cell marker, and one or more agents that modulate immunoregulatory pathways in the subject. Generally at least one agent that modifies immunoregulatory signaling blocks CD47 signaling. Optionally, an agonist of an immune costimulatory molecule, e.g. CD137, may be included in the combination of agents. Following ablation, and after a period of time sufficient to substantially eliminate the stem cell ablative agents from the patient circulation, exogenous stem cells are introduced to the patient, where the exogenous stem cells occupy the same niche as the ablated endogenous stem cells. Exogenous stem cells may be autologous, allogeneic, or xenogeneic relative to the patient.

The period of time required for clearance of the ablative agent may be empirically determined, or may be based on prior experience of the pharmacokinetics of the agent. Where the agent is an antibody, determination can be conveniently monitored by containing stem cells with recipient serum, and determining the presence of antibodies that bind to the stem cells. Alternatively, patient serum may be monitored for the presence of stem cell selective growth inhibition. The time for clearance is usually the time sufficient for the level of ablative agent to decrease as least about 10-fold from peak levels, usually at least about 100-fold, 1000-fold, 10,000-fold, or more. It is preferable to introduce the donor stem cells within the empty niche "window" following ablation, usually within about 3 days, about 2 days, about 1 day, or at the time of clearance.

It is an objective of the present invention to provide a new clinically applicable method of stem cell transplantation which facilitates engraftment and reconstitutes immunocompetence of the recipient without requiring radiotherapy or chemotherapy, or development of GVHD or graft rejection. Aspects of the present invention are based on the discovery that a depletion of the endogenous stem cell niche that facilitates efficient engraftment of hematopoietic stem cells (HSCs) is accomplished by combining the use of an agent that targets the endogenous stem cells, e.g. anti-CD117 antibody, with an agent that enhances the killing of endogenous stem cells by blocking the interaction of CD47 and SIRPα. Optionally, an agonist of CD137 is also included in the method. In particular, the present invention combines this improved selective ablation of endogenous stem cells, in combination with the administration to the recipient of exogenous stem cells, resulting in efficient, long-term engraftment and tolerance.

To facilitate an understanding of the invention, a number of terms are defined below.

Before the present active agents and methods are described, it is to be understood that this invention is not limited to the particular methodology, products, apparatus and factors described, as such methods, apparatus and formulations may, of course, vary. It is also to be understood that the terminology used herein is for the purpose of describing particular embodiments only, and is not intended to limit the scope of the present invention which will be limited only by appended claims.

It must be noted that as used herein and in the appended claims, the singular forms "a," "and," and "the" include plural referents unless the context clearly dictates otherwise. Thus, for example, reference to "a drug candidate" refers to one or mixtures of such candidates, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Generally, conventional methods of protein synthesis, recombinant cell culture and protein isolation, and recombinant DNA techniques within the skill of the art are employed in the present invention. Such techniques are explained fully in the literature, see, e.g., Maniatis, Fritsch & Sambrook, Molecular Cloning: A Laboratory Manual (1982); Sambrook, Russell and Sambrook, Molecular Cloning: A Laboratory Manual (2001); Harlow, Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

Definitions

Anti-CD47 agent. CD47 is a broadly expressed transmembrane glycoprotein with a single Ig-like domain and five membrane spanning regions, which functions as a cellular ligand for SIRPα with binding mediated through the NH2-terminal V-like domain of SIRPα. SIRPα is expressed primarily on myeloid cells, including macrophages, granulocytes, myeloid dendritic cells (DCs), mast cells, and their precursors, including hematopoietic stem cells. Structural determinants on SIRPα that mediate CD47 binding are discussed by Lee et al. (2007) J. Immunol. 179:7741-7750; Hatherley et al. (2008) Mol Cell. 31(2):266-77; Hatherley et al. (2007) J. B. C. 282:14567-75; and the role of SIRPα cis dimerization in CD47 binding is discussed by Lee et al. (2010) J. B. C. 285:37953-63. In keeping with the role of CD47 to inhibit phagocytosis of normal cells, there is evidence that it is transiently upregulated on hematopoietic stem cells (HSCs) and progenitors just prior to and during their migratory phase, and that the level of CD47 on these cells determines the probability that they are engulfed in vivo.

As used herein, the term "anti-CD47 agent" or "agent that provides for CD47 blockade" refers to any agent that reduces the binding of CD47 (e.g., on a target cell) to SIRPα (e.g., on a phagocytic cell). Non-limiting examples of suitable anti-CD47 reagents include SIRPα reagents, including without limitation high affinity SIRPα polypeptides, anti-SIRPα antibodies, soluble CD47 polypeptides, and anti-CD47 antibodies or antibody fragments. In some embodiments, a suitable anti-CD47 agent (e.g. an anti-CD47 antibody, a SIRPα reagent, etc.) specifically binds CD47 to reduce the binding of CD47 to SIRPα.

In some embodiments, a suitable anti-CD47 agent (e.g., an anti-SIRPα antibody, a soluble CD47 polypeptide, etc.) specifically binds SIRPα to reduce the binding of CD47 to SIRPα. A suitable anti-CD47 agent that binds SIRPα does not activate SIRPα (e.g., in the SIRPα-expressing phagocytic cell). The efficacy of a suitable anti-CD47 agent can be assessed by assaying the agent. In an exemplary assay, target cells are incubated in the presence or absence of the candidate agent. An agent for use in the methods of the invention will up-regulate phagocytosis by at least 5% (e.g., at least 10%, at least 20%, at least 30%, at least 40%, at least 50%, at least 60%, at least 70%, at least 80%, at least 90%, at least 100%, at least 120%, at least 140%, at least 160%, at least 180%, at least 200%, at least 500%, at least 1000%) compared to phagocytosis in the absence of the agent. Similarly, an in vitro assay for levels of tyrosine phosphorylation of SIRPα will show a decrease in phosphorylation by at least 5% (e.g., at least 10%, at least 15%, at least 20%, at least 30%, at least 40%, at least 50%, at least 60%, at least 70%, at least 80%, at least 90%, or 100%) compared to phosphorylation observed in absence of the candidate agent.

In some embodiments, the anti-CD47 agent does not activate CD47 upon binding. When CD47 is activated, a process akin to apoptosis (i.e., programmed cell death) may occur (Manna and Frazier, Cancer Research, 64, 1026-1036, Feb. 1, 2004). Thus, in some embodiments, the anti-CD47 agent does not directly induce cell death of a CD47-expressing cell.

SIRPα reagent. A SIRPα reagent comprises the portion of SIRPα that is sufficient to bind CD47 at a recognizable affinity, which normally lies between the signal sequence and the transmembrane domain, or a fragment thereof that retains the binding activity. A suitable SIRPα reagent reduces (e.g., blocks, prevents, etc.) the interaction between the native proteins SIRPα and CD47. The SIRPα reagent will usually comprise at least the d1 domain of SIRPα.

In some embodiments, a subject anti-CD47 agent is a "high affinity SIRPα reagent", which includes SIRPα-derived polypeptides and analogs thereof (e.g., CV1-hIgG4, and CV1 monomer). High affinity SIRPα reagents are described in international application PCT/US13/21937, which is hereby specifically incorporated by reference. High affinity SIRPα reagents are variants of the native SIRPα protein. The amino acid changes that provide for increased affinity are localized in the d1 domain, and thus high affinity SIRPα reagents comprise a d1 domain of human SIRPα, with at least one amino acid change relative to the wild-type sequence within the d1 domain. Such a high affinity SIRPα reagent optionally comprises additional amino acid sequences, for example antibody Fc sequences; portions of the wild-type human SIRPα protein other than the d1 domain, including without limitation residues 150 to 374 of the native protein or fragments thereof, usually fragments contiguous with the d1 domain; and the like. High affinity SIRPα reagents may be monomeric or multimeric, i.e. dimer, trimer, tetramer, etc. In some embodiments, a high affinity SIRPα reagent is soluble, where the polypeptide lacks the SIRPα transmembrane domain and comprises at least one amino acid change relative to the wild-type SIRPα sequence, and wherein the amino acid change increases the affinity of the SIRPα polypeptide binding to CD47, for example by decreasing the off-rate by at least 10-fold, at least 20-fold, at least 50-fold, at least 100-fold, at least 500-fold, or more.

Optionally the SIRPα reagent is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules.

Anti-CD47 antibodies. In some embodiments, a subject anti-CD47 agent is an antibody that specifically binds CD47 (i.e., an anti-CD47 antibody) and reduces the interaction between CD47 on one cell (e.g., an infected cell) and SIRPα on another cell (e.g., a phagocytic cell). In some embodiments, a suitable anti-CD47 antibody does not activate CD47 upon binding. Some anti-CD47 antibodies do not reduce the binding of CD47 to SIRPα (and are therefore not considered to be an "anti-CD47 agent" herein) and such an antibody can be referred to as a "non-blocking anti-CD47 antibody." A suitable anti-CD47 antibody that is an "anti-CD47 agent" can be referred to as a "CD47-blocking antibody". Non-limiting examples of suitable antibodies include clones B6H12, 5F9, 8B6, and C3 (for example as described in International Patent Publication WO 2011/143624, herein specifically incorporated by reference). Suitable anti-CD47 antibodies include fully human, humanized or chimeric versions of such antibodies. Humanized antibodies (e.g., hu5F9-G4) are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Anti-SIRPα antibodies. In some embodiments, a subject anti-CD47 agent is an antibody that specifically binds SIRPα (i.e., an anti-SIRPα antibody) and reduces the interaction between CD47 on one cell (e.g., an infected cell) and SIRPα on another cell (e.g., a phagocytic cell). Suitable anti-SIRPα antibodies can bind SIRPα without activating or stimulating signaling through SIRPα because activation of SIRPα would inhibit phagocytosis. Instead, suitable anti-SIRPα antibodies facilitate the preferential phagocytosis of inflicted cells over normal cells. Those cells that express higher levels of CD47 (e.g., infected cells) relative to other cells (non-infected cells) will be preferentially phagocytosed. Thus, a suitable anti-SIRPα antibody specifically binds SIRPα (without activating/stimulating enough of a signaling response to inhibit phagocytosis) and blocks an interaction between SIRPα and CD47. Suitable anti-SIRPα antibodies include fully human, humanized or chimeric versions of such antibodies. Humanized antibodies are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Soluble CD47 polypeptides. In some embodiments, a subject anti-CD47 agent is a soluble CD47 polypeptide that specifically binds SIRPα and reduces the interaction between CD47 on one cell (e.g., an infected cell) and SIRPα on another cell (e.g., a phagocytic cell). A suitable soluble CD47 polypeptide can bind SIRPα without activating or stimulating signaling through SIRPα because activation of SIRPα would inhibit phagocytosis. Instead, suitable soluble CD47 polypeptides facilitate the preferential phagocytosis of infected cells over non-infected cells. Those cells that express higher levels of CD47 (e.g., infected cells) relative to normal, non-target cells (normal cells) will be preferentially phagocytosed. Thus, a suitable soluble CD47 polypeptide specifically binds SIRPα without activating/stimulating enough of a signaling response to inhibit phagocytosis.

In some cases, a suitable soluble CD47 polypeptide can be a fusion protein (for example as structurally described in US Patent Publication US20100239579, herein specifically incorporated by reference). However, only fusion proteins that do not activate/stimulate SIRPα are suitable for the methods provided herein. Suitable soluble CD47 polypeptides also include any peptide or peptide fragment comprising variant or naturally existing CD47 sequences (e.g., extracellular domain sequences or extracellular domain variants) that can specifically bind SIRPα and inhibit the interaction between CD47 and SIRPα without stimulating enough SIRPα activity to inhibit phagocytosis.

In certain embodiments, soluble CD47 polypeptide comprises the extracellular domain of CD47, including the signal peptide, such that the extracellular portion of CD47 is typically 142 amino acids in length. The soluble CD47 polypeptides described herein also include CD47 extracellular domain variants that comprise an amino acid sequence at least 65%-75%, 75%-80%, 80-85%, 85%-90%, or 95%-99% (or any percent identity not specifically enumerated between 65% to 100%), which variants retain the capability to bind to SIRPα without stimulating SIRPα signaling.

In certain embodiments, the signal peptide amino acid sequence may be substituted with a signal peptide amino acid sequence that is derived from another polypeptide (e.g., for example, an immunoglobulin or CTLA4). For example, unlike full-length CD47, which is a cell surface polypeptide that traverses the outer cell membrane, the soluble CD47 polypeptides are secreted; accordingly, a polynucleotide encoding a soluble CD47 polypeptide may include a nucleotide sequence encoding a signal peptide that is associated with a polypeptide that is normally secreted from a cell.

In other embodiments, the soluble CD47 polypeptide comprises an extracellular domain of CD47 that lacks the signal peptide. As described herein, signal peptides are not exposed on the cell surface of a secreted or transmembrane protein because either the signal peptide is cleaved during translocation of the protein or the signal peptide remains anchored in the outer cell membrane (such a peptide is also called a signal anchor). The signal peptide sequence of CD47 is believed to be cleaved from the precursor CD47 polypeptide in vivo.

In other embodiments, a soluble CD47 polypeptide comprises a CD47 extracellular domain variant. Such a soluble CD47 polypeptide retains the capability to bind to SIRPα without stimulating SIRPα signaling. The CD47 extracellular domain variant may have an amino acid sequence that is at least 65%-75%, 75%-80%, 80-85%, 85%-90%, or 95%-99% identical (which includes any percent identity between any one of the described ranges) to the native CD47 sequence.

Stem cell markers. Exemplary markers for antibody mediated ablation of human hematopoietic stem cells include CD34; CD90 (thy-1); CD59; CD110 (c-mpl); c-kit (CD-117); etc. Markers useful for the ablation of mesodermal stem cells include FcγRII, FcγRIII, Thy-1, CD44, VLA-4α, LFA-1β, HSA, ICAM-1, CD45, Aa4.1, Sca-1, etc. Neural crest stem cells may be positively selected with antibodies specific for low-affinity nerve growth factor receptor (LNGFR). Neural stem/progenitor cells have been described in the art, and their use in a variety of therapeutic protocols has been widely discussed. For example, inter alia, Uchida et al. (2000) Proc Natl Acad Sci USA. 97(26):14720-5. U.S. Pat. No. 6,638,501, Bjornson et al.; U.S. Pat. No. 6,541,255, Snyder et al.; U.S. Pat. No. 6,498,018, Carpenter; U.S. Patent Application 20020012903, Goldman et al.; Palmer et al. (2001) Nature 411(6833):42-3; Palmer et al. (1997) Mol Cell Neurosci. 8(6):389-404; Svendsen et al. (1997) Exp. Neurol. 148(1):135-46 and Shihabuddin (1999) Mol Med Today. 5(11):474-80; each herein specifically incorporated by reference. Human mesenchymal stem cells may be ablated using the markers such as SH2 (CD105), SH3 and SH4 and Stro-1.

In one embodiment of the invention, the marker for ablation is c-kit (CD117). CD117 is a receptor tyrosine kinase type III, which binds to stem cell factor (a substance that causes certain types of cells to grow), also known as "steel factor" or "c-kit ligand". When this receptor binds to stem cell factor (SCF) it forms a dimer that activates its intrinsic tyrosine kinase activity, that in turn phosphorylates and activates signal transduction molecules that propagate the signal in the cell. See, for example, the human refseq entries Genbank NM_000222; NP_000213. CD117 is an important cell surface marker used to identify certain types of hematopoietic (blood) progenitors in the bone marrow. Hematopoietic stem cells (HSC), multipotent progenitors (MPP), and common myeloid progenitors (CMP) express high levels of CD117. A number of antibodies that specifically bind human CD117 are known in the art and commercially available, including without limitation 2B8, ACK2, YB5-B8, 57A5, 104D2, etc.

Immunoregulatory signaling molecules. In addition to the CD47/SIRPα axis, immunoregulatory signaling molecules may include costimulatory polypeptides expressed on immune cells. Activation, i.e. agonism, of the costimulatory molecule enhances the effector cell function. Many such costimulatory molecules are members of the tumor necrosis factor receptor family (TNFR), e.g. OX40, GITR, CD30, ICOS, etc. TNFR-related molecules do not have any known enzymatic activity and depend on the recruitment of cytoplasmic proteins for the activation of downstream signaling pathways.

A costimulatory molecule of interest is CD137, which may also be referred to as Ly63, ILA or 4-1BB, and which is a member of the tumor necrosis factor (TNF) receptor family. Members of this receptor family and their structurally related ligands are important regulators of a wide variety of physiologic processes and play an important role in the regulation of immune responses. CD137 is expressed by activated NK cells, T and B lymphocytes and monocytes/macrophages. The gene encodes a 255-amino acid protein with 3 cysteine-rich motifs in the extracellular domain (characteristic of this receptor family), a transmembrane region, and a short N-terminal cytoplasmic portion containing potential phosphorylation sites. Expression in primary cells is strictly activation dependent. The ligand for the receptor is TNFSF9. Human CD137 is reported to bind only to its ligand. Agonists include the native ligand (TNFSF9), aptamers (see McNamara et al. (2008) J. Clin. Invest. 118: 376-386), and antibodies.

Agonists includes the native ligands, as described above, aptamers, antibodies specific for an inducible costimulatory molecule that activate the receptor, and derivatives, variants, and biologically active fragments of antibodies that selectively bind to a costimulatory molecule. A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, preferably at least about 95%, more preferably at least about 99%. The variant polypeptides can be naturally or non-naturally glycosylated, i.e., the polypeptide has a glycosylation pattern that differs from the glycosylation pattern found in the corresponding naturally occurring protein.

Fragments of the ligand or antibodies specific for a costimulatory molecule, particularly biologically active fragments and/or fragments corresponding to functional domains, are of interest. Fragments of interest will typically be at least about 10 aa to at least about 15 aa in length, usually at least about 50 aa in length, but will usually not exceed about 200 aa in length, where the fragment will have a contiguous stretch of amino acids that is identical to the polypeptide from which it is derived. A fragment "at least 20 aa in length," for example, is intended to include 20 or more contiguous amino acids from, for example, an antibody specific for CD137, or from TNFSF9. In this context "about" includes the particularly recited value or a value larger or smaller by several (5, 4, 3, 2, or 1) amino acids. The protein variants described herein are encoded by polynucleotides that are within the scope of the invention. The genetic code can be used to select the appropriate codons to construct the corresponding variants. The polynucleotides may be used to produce polypeptides, and these polypeptides may be used to produce antibodies by known methods. A "fusion" polypeptide is a polypeptide comprising a polypeptide or portion (e.g., one or more domains) thereof fused or bonded to heterologous polypeptide.

In some embodiments, the costimulatory molecule agonist is an antibody. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. Antibodies utilized in the present invention may be polyclonal antibodies, although monoclonal antibodies are preferred because they may be reproduced by cell culture or recombinantly, and can be modified to reduce their antigenicity.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies. The term "antibody" also includes antigen binding forms of antibodies, including fragments with antigen-binding capability (e.g., Fab', F(ab')$_2$, Fab, Fv and rIgG. The term also refers to recombinant single chain Fv fragments (scFv). The term antibody also includes bivalent or bispecific molecules, diabodies, triabodies, and tetrabodies.

Selection of antibodies for endogenous stem cell ablation may be based on a variety of criteria, including selectivity, affinity, cytotoxicity, etc. The phrase "specifically (or selectively) binds" to an antibody or "specifically (or selectively) immunoreactive with," when referring to a protein or peptide, refers to a binding reaction that is determinative of the presence of the protein, in a heterogeneous population of proteins and other biologics. Thus, under designated immunoassay conditions, the specified antibodies bind to a particular protein sequences at least two times the background and more typically more than 10 to 100 times background. In general, antibodies of the present invention bind antigens on the surface of target cells in the presence of effector cells (such as natural killer cells or macrophages). Fc receptors on effector cells recognize bound antibodies. The cross-linking of Fc receptors signals the effector cells to kill the target cells by cytolysis or apoptosis. In one embodiment, the induction is achieved via antibody-dependent cellular cytotoxicity (ADCC). In alternative embodiments, the antibodies are active in growth inhibition of the targeted cells, an ablation is achieved by interfering with growth factor signaling, e.g. antibodies specific for growth factor receptors such as c-kit.

An antibody immunologically reactive with a particular antigen can be generated by recombinant methods such as selection of libraries of recombinant antibodies in phage or similar vectors, or by immunizing an animal with the antigen or with DNA encoding the antigen. Methods of preparing polyclonal antibodies are known to the skilled artisan. The antibodies may, alternatively, be monoclonal antibodies. Monoclonal antibodies may be prepared using hybridoma methods. In a hybridoma method, an appropriate host animal is typically immunized with an immunizing agent to elicit lymphocytes that produce or are capable of producing antibodies that will specifically bind to the immunizing agent. Alternatively, the lymphocytes may be immunized in vitro. The lymphocytes are then fused with an immortalized cell line using a suitable fusing agent, such as polyethylene glycol, to form a hybridoma cell.

Human antibodies can be produced using various techniques known in the art, including phage display libraries. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire.

Antibodies also exist as a number of well-characterized fragments produced by digestion with various peptidases. Thus pepsin digests an antibody below the disulfide linkages in the hinge region to produce F(ab)'$_2$, a dimer of Fab which itself is a light chain joined to $V_H$-$C_{H1}$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries.

A "humanized antibody" is an immunoglobulin molecule which contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin.

Antibodies of interest for ablation may be tested for their ability to induce ADCC (antibody-dependent cellular cytotoxicity). Antibody-associated ADCC activity can be monitored and quantified through detection of either the release of label or lactate dehydrogenase from the lysed cells, or detection of reduced target cell viability (e.g. annexin assay). Assays for apoptosis may be performed by terminal deoxynucleotidyl transferase-mediated digoxigenin-11-dUTP nick end labeling (TUNEL) assay (Lazebnik et al., Nature: 371, 346 (1994). Cytotoxicity may also be detected directly by detection kits known in the art, such as Cytotoxicity Detection Kit from Roche Applied Science (Indianapolis, Ind.). Preferably, the antibodies of the present invention induce at least 10%, 20%, 30%, 40%, 50%, 60%, or 80% cytotoxicity of the target cells.

In some embodiments, the antibody is conjugated to an effector moiety. The effector moiety can be any number of molecules, including labeling moieties such as radioactive labels or fluorescent labels, or can be a cytotoxic moiety. Cytotoxic agents are numerous and varied and include, but are not limited to, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin, auristatin-E and the like. Cytotoxic agents also include radiochemicals made by conjugating radioisotopes to antibodies. Targeting the cytotoxic moiety to transmembrane proteins serves to increase the local concentration of the cytotoxic moiety in the targeted area.

The term stem cell is used herein to refer to a mammalian cell that has the ability both to self-renew, and to generate differentiated progeny (see Morrison et al. (1997) Cell 88:287-298). Generally, stem cells also have one or more of the following properties: an ability to undergo asynchronous, or symmetric replication, that is where the two daughter cells after division can have different phenotypes; extensive self-renewal capacity; capacity for existence in a mitotically quiescent form; and clonal regeneration of all the tissue in which they exist, for example the ability of hematopoietic stem cells to reconstitute all hematopoietic lineages.

Stem cells of interest include hematopoietic stem cells; neural crest stem cells (see Morrison et al. (1999) Cell 96:737-749); mesenchymal stem cells; mesodermal stem cells; etc. The cells of interest are typically mammalian, where the term refers to any animal classified as a mammal, including humans, domestic and farm animals, and zoo, laboratory, sports, or pet animals, such as dogs, horses, cats, cows, mice, rats, rabbits, etc. Preferably, the mammal is human.

For engraftment purposes, a composition comprising stem cells, including, without limitation, hematopoietic stem cells, is administered to a patient. Such methods are well known in the art. The stem cells are optionally, although not necessarily, purified. Abundant reports explore various methods for purification of stem cells and subsequent engraftment, including flow cytometry; an isolex system (Klein et al. (2001) Bone Marrow Transplant. 28(11):1023-9; Prince et al. (2002) Cytotherapy 4(2):137-45); immunomagnetic separation (Prince et al. (2002) Cytotherapy 4(2): 147-55; Handgretinger et al. (2002) Bone Marrow Transplant. 29(9):731-6; Chou et al. (2005) Breast Cancer. 12(3):178-88); and the like. Each of these references is herein specifically incorporated by reference, particularly with respect to procedures, cell compositions and doses for hematopoietic stem cell transplantation.

Hematopoietic stem cells can be obtained by harvesting from bone marrow or from peripheral blood. Bone marrow is generally aspirated from the posterior iliac crests while the donor is under either regional or general anesthesia. Additional bone marrow can be obtained from the anterior iliac crest. A dose of $1\times10^8$ and $2\times10^8$ marrow mononuclear cells per kilogram is generally considered desirable to establish engraftment in autologous and allogeneic marrow transplants, respectively. Bone marrow can be primed with granulocyte colony-stimulating factor (G-CSF; filgrastim [Neupogen]) to increase the stem cell count.

Mobilization of stem cells from the bone marrow into peripheral blood by cytokines such as G-CSF or GM-CSF has led to the widespread adoption of peripheral blood progenitor cell collection by apheresis for hematopoietic stem cell transplantation. The dose of G-CSF used for mobilization is 10 µg/kg/day. In autologous donors who are heavily pretreated, however, doses of up to 40 µg/kg/day can be given. Mozobil may be used In conjunction with G-CSF to mobilize hematopoietic stem cells to peripheral blood for collection.

Current guidelines indicate that the minimum dose required for engraftment is $1$-$2\times10^8$ $CD34^+$ cells/kg body weight for autologous and allogeneic transplants. Higher doses would result in better engraftment, but doses in the range of $8\times10^8$ may be associated with increased risk of extensive GVHD.

The cells which are employed may be fresh, frozen, or have been subject to prior culture. They may be fetal, neonate, adult, etc. Hematopoietic stem cells may be obtained from fetal liver, bone marrow, blood, particularly G-CSF or GM-CSF mobilized peripheral blood, or any other conventional source. Cells for engraftment are optionally isolated from other cells, where the manner in which the stem cells are separated from other cells of the hematopoietic or other lineage is not critical to this invention. If desired, a substantially homogeneous population of stem or progenitor cells may be obtained by selective isolation of cells free of markers associated with differentiated cells, while displaying epitopic characteristics associated with the stem cells.

Cells may be genetically altered in order to introduce genes useful in the differentiated cell, e.g. repair of a genetic defect in an individual, selectable marker, etc., or genes useful in selection against undifferentiated ES cells. Cells may also be genetically modified to enhance survival, control proliferation, and the like. Cells may be genetically altering by transfection or transduction with a suitable vector, homologous recombination, or other appropriate technique, so that they express a gene of interest. In one embodiment, cells are transfected with genes encoding a telomerase catalytic component (TERT), typically under a heterologous promoter that increases telomerase expression beyond what occurs under the endogenous promoter, (see International Patent Application WO 98/14592). In other embodiments, a selectable marker is introduced, to provide for greater purity of the desired differentiating cell. Cells may be genetically altered using vector containing supernatants over an 8-16 h period, and then exchanged into growth medium for 1-2 days. Genetically altered cells are selected using a drug selection agent such as puromycin, G418, or blasticidin, and then recultured.

The cells of this invention can also be genetically altered in order to enhance their ability to be involved in tissue regeneration, or to deliver a therapeutic gene to a site of administration. A vector is designed using the known encoding sequence for the desired gene, operatively linked to a promoter that is constitutive, pan-specific, specifically active in a differentiated cell type, etc. Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold. Various promoters are known that are induced in different cell types.

Many vectors useful for transferring exogenous genes into target mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc. For modification of stem cells, lentiviral vectors are preferred. Lentiviral vectors such as those based on HIV or FIV gag sequences can be used to transfect non-dividing cells, such as the resting phase of human stem cells. Combinations of retroviruses and an appropriate packaging line may also find use, where the capsid proteins will be functional for infecting the target cells. Usually, the cells and virus will be incubated for at least about 24 hours in the culture medium. The cells are then allowed to grow in the culture medium for short intervals in some applications, e.g. 24-73 hours, or for at least two weeks, and may be allowed to grow for five weeks or more, before analysis. Commonly used retroviral vectors are "defective", i.e. unable to produce viral proteins required for productive infection. Replication of the vector requires growth in the packaging cell line. The vectors may include genes that must later be removed, e.g. using a recombinase system such as Cre/Lox, or the cells that express them destroyed, e.g. by including genes that allow selective toxicity such as herpesvirus TK, bcl-xs, etc.

A "patient" for the purposes of the present invention includes both humans and other animals, particularly mammals, including pet and laboratory animals, e.g. mice, rats, rabbits, etc. Thus the methods are applicable to both human therapy and veterinary applications. In one embodiment the patient is a mammal, preferably a primate. In other embodiments the patient is human.

Additional terms. The terms "treatment", "treating", "treat" and the like are used herein to generally refer to obtaining a desired pharmacologic and/or physiological effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with cancer, those with an infection, etc.) as well as those in which prevention is desired (e.g., those with increased susceptibility to cancer, those with an increased likelihood of infection, those suspected of having cancer, those suspected of harboring an infection, etc.).

Methods for Engraftment

The methods of the invention provide for improved engraftment of stem cells after transplantation into a recipient. The recipient may be immunocompetent, and the transplantation may be performed in the absence of myeloablative conditioning, i.e. in the absence of radiation and/or chemotherapeutic drugs. The recipient is conditioned with the combined administration of an effective dose of an agent, e.g. an antibody, specific for a stem cell marker, and an agent that blocks CD47 interaction with SIRPα. Optionally the method also comprises administration of an agonist of a an immunoregulatory molecule, e.g. CD137. The conditioning regimen of the invention selectively ablates endogenous stem cells. Following the conditioning regimen, an effective dose of a cellular composition comprising exogenous stem cells is administered to the recipient. The stem cells may be autologous, allogeneic or xenogeneic.

In some embodiments the stem cells are hematopoietic stem cells. Agents of interest agent specific for a hematopoietic stem cells include, without limitation, antibodies that bind to CD117. An effective dose of antibody is the dose that, when combined with the anti-CD47 agent, depletes endogenous hematopoietic stem cells by at least 10-fold, at least 100-fold, at least 1000-fold, at least 100,000-fold or more. The effective dose will depend on the individual and the specific antibody, but will generally be at least about 50 μg/kg body weight, at least about 250 μg/kg, at least about 500 μg/kg, at least about 750 μg/kg, at least about 1 mg/kg, and up to about 2.5 mg/kg, up to about 5 mg/kg, up to about 7.5 mg/kg, up to about 10 mg/kg, up to about 15 mg/kg, up to about 25 mg/kg, up to about 50 mg/kg, up to about 100 mg/kg.

The anti-CD47 agent is provided in a dose that, when combined with the stem cell specific agent, depletes endogenous hematopoietic stem cells by at least 10-fold, at least 100-fold, at least 1000-fold, at least 100,000-fold or more. The effective dose will depend on the individual and the specific agent, but will generally be at least about 50 μg/kg body weight, at least about 250 μg/kg, at least about 500 μg/kg, at least about 750 μg/kg, at least about 1 mg/kg, and up to about 2.5 mg/kg, up to about 5 mg/kg, up to about 7.5 mg/kg, up to about 10 mg/kg, up to about 15 mg/kg, up to about 25 mg/kg, up to about 50 mg/kg, up to about 100 mg/kg. In some embodiments the agent is a CV1 (high affinity SIRPα) monomer or CV1 microbody dimer.

The CD137 agonist, when present, is provided in a dose that, when combined with the stem cell specific agent and the anti-CD47 agent, depletes endogenous hematopoietic stem cells by at least 2-fold, at least 5-fold, at least 10-fold, or more relative to the method in the absence of the CD137 agonist. The effective dose will depend on the individual and the specific agent, but will generally be at least about 50 μg/kg body weight, at least about 250 μg/kg, at least about 500 μg/kg, at least about 750 μg/kg, at least about 1 mg/kg, and up to about 2.5 mg/kg, up to about 5 mg/kg, up to about 7.5 mg/kg, up to about 10 mg/kg, up to about 15 mg/kg, up to about 25 mg/kg, up to about 50 mg/kg, up to about 100 mg/kg. In some embodiments the agent is an agonist antibody specific for CD137.

The conditioning agents, which may be provided in the absence of myeloablative radiation or chemotherapy, are administered daily, twice daily, every other day, every third day, etc. for a period of time sufficient to effect the desired ablation of endogenous stem cells, at least about 1 day, up to about 2 days, up to about 3, 4, 5, 6, 7, 8 or more days. In some embodiments from 4-7 days is sufficient. The agents may be formulated together or separately, but are administered concomitantly. "Concomitant" and "concomitantly" as used herein refer to the administration of at least two agents, or at least three agents, to a patient either simultaneously or within a time period during which the effects of the first administered agent are still operative in the patient. Thus, if the first drug is, e.g., anti-CD117 antibody and the second drug is a soluble SIRPα, the concomitant administration of the second agent can occur one to two days after the first, preferably within one to seven days, after the administration of the first agent. Where a CD137 agonist is included, it may be administered with one, two, three, four, five days of the anti-CD117 antibody, and may be co-formulated or separately formulated with the anti-CD47 agent.

The infusion of either bone marrow or peripheral blood progenitor cells (PBPCs) is a relatively simple process that is performed at the bedside. The bone marrow product is generally used fresh and is infused through a central vein over a period of several hours. Autologous products are frequently cryopreserved; if so they are thawed at the bedside and infused rapidly over a period of several minutes. The dose of HSC is at least about $10^5$ CD34+ cells/kg body weight, at least about $0.5 \times 10^6$, at least about $10^6$, and up to about $2.5 \times 10^6$, $5 \times 10^6$, $7.5 \times 10^6$, $10^7$ CD34+ cells/kg body weight.

Where the donor is allogeneic to the recipient, the HLA type of the donor and recipient may be tested for a match. Traditionally, the loci critical for matching are HLA-A, HLA-B, and HLA-DR. HLA-C and HLA-DQ are also now considered when determining the appropriateness of a donor. A completely matched sibling donor is generally considered the ideal donor. For unrelated donors, a complete match or a single mismatch is considered acceptable for most transplantation, although in certain circumstances, a greater mismatch is tolerated. Preferably matching is both serologic and molecular. Where the donor is umbilical cord blood the degree of tolerable HLA disparity is much greater, and a match of 3-4 out of the 6 HLA-A, HLA-B and HLA-DRB1 antigens is sufficient for transplantation. Immunocompetent donor T cells may be removed using a variety of methods to reduce or eliminate the possibility that graft versus host disease (GVHD) will develop.

For positive selection of $CD34^+$ cells, commercial instruments can be employed to remove the desired cells, using solid-phase, anti-CD34 monoclonal antibodies. With negative selection, anticancer monoclonal antibodies can be used to remove tumor cells, leaving stem cells in the graft.

For ablation, the ablative agents are formulated in a pharmaceutical composition. The exact dose will depend on the purpose of the treatment, and will be ascertainable by one skilled in the art using known techniques (e.g., Ansel et al., Pharmaceutical Dosage Forms and Drug Delivery; Lieberman, Pharmaceutical Dosage Forms (vols. 1-3, 1992), Dekker, ISBN 0824770846, 082476918X, 0824712692, 0824716981; Lloyd, The Art, Science and Technology of Pharmaceutical Compounding (1999); and Pickar, Dosage Calculations (1999)). As is known in the art, adjustments for patient condition, systemic versus localized delivery, as well as the age, body weight, general health, sex, diet, time of administration, drug interaction and the severity of the condition may be necessary, and will be ascertainable with routine experimentation by those skilled in the art.

The administration of the agents can be done in a variety of ways as discussed above, including, but not limited to, orally, subcutaneously, intravenously, intranasally, transdermally, intraperitoneally, intramuscularly, intrapulmonary, vaginally, rectally, or intraocularly.

In one embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly useful are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that compositions of the invention when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The compositions for administration will commonly comprise an antibody or other ablative agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

The compositions containing ablative agents, e.g. antibodies, soluble SIRPα, etc. can be administered for therapeutic treatment. Compositions are administered to a patient in an amount sufficient to substantially ablate targeted endogenous stem cells, as described above. An amount adequate to accomplish this is defined as a "therapeutically effective dose." Single or multiple administrations of the compositions may be administered depending on the dosage and frequency as required and tolerated by the patient. The particular dose required for a treatment will depend upon the medical condition and history of the mammal, as well as other factors such as age, weight, gender, administration route, efficiency, etc.

In the methods of the invention, the agents are administered as a short course of therapy prior to transplantation. Usually the treatment is completed at least about one week prior to transplantation, at least about 5 days prior to transplantation, at least about 3 days prior to transplantation. The process may be repeated if necessary, e.g. may be repeated twice, three times, four times, five times, or more, as necessary to clear the niche.

Conditions for Treatment

The indications for stem cell transplantation vary according to disease categories and are influenced by factors such as cytogenetic abnormalities, response to prior therapy, patient age and performance status, disease status (remission vs relapse), disease-specific prognostic factors, availability of a suitable graft source, time of referral, and time to transplant.

Autologous HSCT is currently used to treat the following conditions: Multiple myeloma, Non-Hodgkin lymphoma, Hodgkin disease, Acute myeloid leukemia, Neuroblastoma, Germ cell tumors, Autoimmune disorders—Systemic lupus erythematosus (SLE), systemic sclerosis, Amyloidosis.

Allogenic HSCT is currently used to treat the following disorders: Acute myeloid leukemia, Acute lymphoblastic leukemia, Chronic myeloid leukemia; Chronic lymphocytic leukemia, Myeloproliferative disorders, Myelodysplastic syndromes, Multiple myeloma, Non-Hodgkin lymphoma, Hodgkin disease, Aplastic anemia, Pure red cell aplasia, Paroxysmal nocturnal hemoglobinuria, Fanconi anemia, Thalassemia major, Sickle cell anemia, Severe combined immunodeficiency (SCID), Wiskott-Aldrich syndrome, Hemophagocytic lymphohistiocytosis (HLH), Inborn errors of metabolism—Eg, mucopolysaccharidosis, Gaucher disease, metachromatic leukodystrophies, and adrenoleukodystrophies, Epidermolysis bullosa, Severe congenital neutropenia, Shwachman-Diamond syndrome, Diamond-Blackfan anemia, Leukocyte adhesion deficiency, and the like.

Embodiments of the invention include transplantation into a patient suffering from a genetic blood disorder, where exogenous stem cells of a normal phenotype are transplanted into the patient. Such diseases include, without limitation, the treatment of anemias caused by defective hemoglobin synthesis (hemoglobinopathies).

Sickle cell diseases include HbS Disease; drepanocytic anemia; meniscocytosis. Chronic hemolytic anemia occurring almost exclusively in blacks and characterized by sickle-shaped RBCs caused by homozygous inheritance of Hb S. Homozygotes have sickle cell anemia; heterozygotes are not anemic, but the sickling trait (sicklemia) can be demonstrated in vitro. In Hb S, valine is substituted for glutamic acid in the sixth amino acid of the beta chain. Deoxy-Hb S is much less soluble than deoxy-Hb A; it forms a semisolid gel of rodlike tactoids that cause RBCs to sickle at sites of low $PO_2$. Distorted, inflexible RBCs adhere to vascular endothelium and plug small arterioles and capillaries, which leads to occlusion and infarction. Because sickled RBCs are too fragile to withstand the mechanical trauma of circulation, hemolysis occurs after they enter the circulation. In homozygotes, clinical manifestations are caused by anemia and vaso-occlusive events resulting in tissue ischemia and infarction. Growth and development are impaired, and susceptibility to infection increases. Anemia is usually severe but varies highly among patients. Anemia may be exacerbated in children by acute sequestration of sickled cells in the spleen.

Thalassemias are a group of chronic, inherited, microcytic anemias characterized by defective Hb synthesis and ineffective erythropoiesis, particularly common in persons of Mediterranean, African, and Southeast Asian ancestry. Thalassemia is among the most common inherited hemolytic disorders. It results from unbalanced Hb synthesis caused by decreased production of at least one globin polypeptide chain ($\beta$, $\alpha$, $\gamma$, $\delta$).

Aplastic anemia results from a loss of RBC precursors, either from a defect in stem cell pool or an injury to the microenvironment that supports the marrow, and often with borderline high MCV values. The term aplastic anemia commonly implies a panhypoplasia of the marrow with associated leukopenia and thrombocytopenia.

Combined immunodeficiency is a group of disorders characterized by congenital and usually hereditary deficiency of both B- and T-cell systems, lymphoid aplasia, and thymic dysplasia. The combined immunodeficiencies include severe combined immunodeficiency, Swiss agammaglobulinemia, combined immunodeficiency with adenosine deaminase or nucleoside phosphorylase deficiency, and combined immunodeficiency with immunoglobulins (Nezelof syndrome). Most patients have an early onset of infection with thrush, pneumonia, and diarrhea. If left untreated, most die before age 2. Most patients have profound deficiency of B cells and immunoglobulin. The following are characteristic: lymphopenia, low or absent T-cell levels, poor proliferative response to mitogens, cutaneous anergy, an absent thymic shadow, and diminished lymphoid tissue. *Pneumocystis* pneumonia and other opportunistic infections are common.

EXPERIMENTAL

Example 1

HSC Transplantation in an Immunocompetent Host without Radiation or Chemotherapy Hematopoietic stem cell (HSC) transplantation can treat diverse diseases of the blood system, including hematologic malignancies, anemias, and autoimmune disorders. However, patients must undergo toxic conditioning regimens such as chemotherapy and/or radiation to eliminate host HSCs and enable donor HSC engraftment. We have previously shown that monoclonal anti c-Kit antibody depletes HSCs from bone marrow niches and facilitates donor HSC engraftment in immune-deficient mice. Here we demonstrate that anti-c-Kit antibody depletes HSCs in an Fc dependent manner, implying the involvement of effector cells, and that the blockade of the 'don't eat me' molecule CD47 synergizes with anti-c-Kit antibody as a conditioning agent in immunocompetent mice. The combined treatment leads to elimination of >99% of host HSCs and robust multilineage blood reconstitution following HSC transplantation in immunocompetent mice. This targeted conditioning with biologic agents has the potential to transform the practice of HSC transplantation and extend its use to a wider spectrum of patients.

Hematopoietic stem cells (HSCs) are multipotent stem cells that give rise to all cells of the blood system for the life of an individual. HSCs reside in specialized 'niches' within the bone marrow that allow them to self-renew and remain in an undifferentiated state. Transplantation of HSCs into a host can regenerate a healthy blood system, and in so doing, cure many life threatening blood disorders, autoimmune diseases, and hematologic malignancies. However, for successful engraftment of exogenous HSCs to engraft, two obstacles must be overcome. Firstly, donor HSCs must escape immune rejection by the recipient, and secondly, the transplanted cells must have access to niche space within the recipient bone marrow.

The current conditioning regimes of radiation and/or chemotherapy simultaneously immunosuppresses the recipient by lymphoablation and kills resident HSCs to free bone marrow niches. However these procedures also result in non-specific injury to other tissues and can cause secondary malignancies. So we sought transplant conditioning regimens lacking chemo- or radiotherapy. Consequently, HSC transplantation is reserved for those with life-threatening disorders where the benefits are thought to outweigh the risks of the procedure. Safer and more targeted conditioning protocols could both improve the safety of transplantation and extend the existing clinical utility of this powerful form of cell therapy. Allogeneic HSC transplantation results in GvH-free replacement of diseased hematopoietic cells, as well as inducing permanent transplantation tolerance of cells, tissues, or organs from the HSC donor, and therefore represents the platform upon which regenerative medicine rests.

HSCs and downstream hematopoietic progenitors express c-Kit (CD117), a dimeric transmembrane receptor tyrosine kinase. Signaling engaged by c-Kit ligand (KL) is essential for numerous HSC functions, including homing, proliferation, adhesion, maintenance, and survival. The critical role of c-Kit in HSC regulation is evidenced in W41/W41 mice that harbor hypomorphic c-Kit alleles. W41/W41 mice have reduced numbers of HSCs and can be robustly reconstituted by exogenous HSCs with minimal radiation. Similarly, immunocompromised c-Kit mutant mice can be engrafted by human HSCs without any irradiation. Furthermore, targeted deletion of KL in perivascular cells results in loss of HSCs in vivo, thus establishing the requirement for c-Kit ligand in addition to the c-Kit receptor. Administration of a monoclonal anti-mouse c-Kit antibody (ACK2) into immunocompromised $Rag2^{-/-}\gamma c^{-/-}$ and $Rag2^{-/-}$ mice depletes host HSCs and enables exogenous HSCs to engraft (FIG. 4a). Similarly, administration of the ACK2 in utero, eliminates HSCs in developing mouse embryos and permits HSC engraftment in neonates. However, ACK2 as a single agent is incapable of conditioning immunocompetent adult mice to accept donor HSCs. Low dose radiation is required for ACK2 mediated depletion of HSCs and engraftment in immunocompetent mice.

Anti-c-Kit antibodies deplete HSCs in an Fc-dependent manner. We first compared the ability of the anti-c-Kit antibody ACK2 to deplete HSCs in wild-type (WT) versus immunodeficient $Rag2^{-/-}c\gamma^{-/-}$ mice. As observed previously, ACK2-mediated depletion of immunophenotypic Lin$^-$Sca-1$^+$c-Kit$^+$CD150$^+$Flt3$^-$CD34$^-$long-term (LT)-HSCs was much greater in $Rag2^{-/-}c\gamma^{-/-}$ than in WT mice (FIG. 4a). In $Rag2^{-/-}c\gamma^{-/-}$ mice, a single 500 µg dose of ACK2 reduced LT-HSC numbers by greater than four orders of magnitude six days after administration. By contrast, in WT mice ACK2 administration produced a modest (<10-fold) decrease in HSCs with complete recovery of the HSC compartment 6-9 days later (FIG. 4a).

To determine if the depletive activity of ACK2 could be enhanced in wild-type animals, we investigated the mechanism of ACK2-mediated HSC clearance. Previously, it was surmised that ACK2 acts primarily by blocking the interaction between c-Kit and KL based on studies that showed comparative lack of effectiveness of 2B8, a different non-blocking anti-c-Kit antibody. However, multiple factors govern antibody efficacy; such as antibody isotype, binding orientation, and receptor internalization, which could also explain the differential activity of 2B8 versus ACK2.

We asked whether ACK2 depletes HSC via effector cell involvement. To address this question, we prepared Fab fragments of ACK2 that lack Fc portion. The Fc portion of an antibody plays a critical role in immune-mediated cell killing including activation of effector cells and phagocytosis of target cells. Administration of ACK2 to $Rag2^{-/-}c\gamma^{-/-}$ mice caused the depletion of HSC in a dose-dependent manner. In contrast, F[ab]' fragment of ACK2 had no discernable effect on HSC frequency, suggesting that ACK2 mediated HSC depletion is Fc receptor dependent (FIG. 4b). To test further whether Fc portion of ACK2 is required for HSC depletion, we exploited the $Fcer1g^{-/-}$ mice that are deficient in the γ chain subunit of the FcγRIII and FcεRI receptor and lack functional ADCC activity of NK cells, and functional phagocytic capacity of macrophages, and neutrophils, and functional allergic activities of mast cells and basophils. Treatment of ACK2 into $Fcer1g^{-/-}$ mice had no effect on HSC number in the BM (FIG. 4c). These data suggest that ACK2 induces depletion of HSCs via Fc effector functions.

Figure 4D:
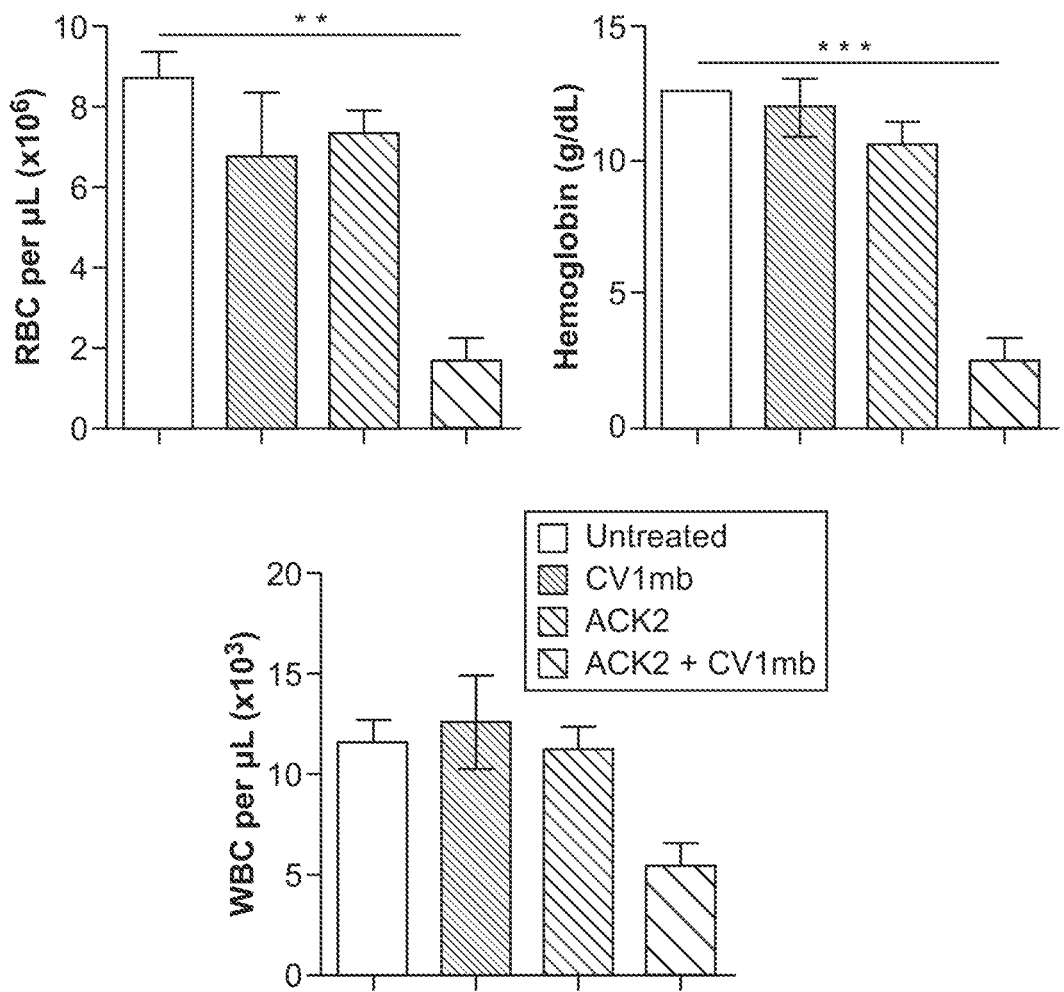
Figure 4E:
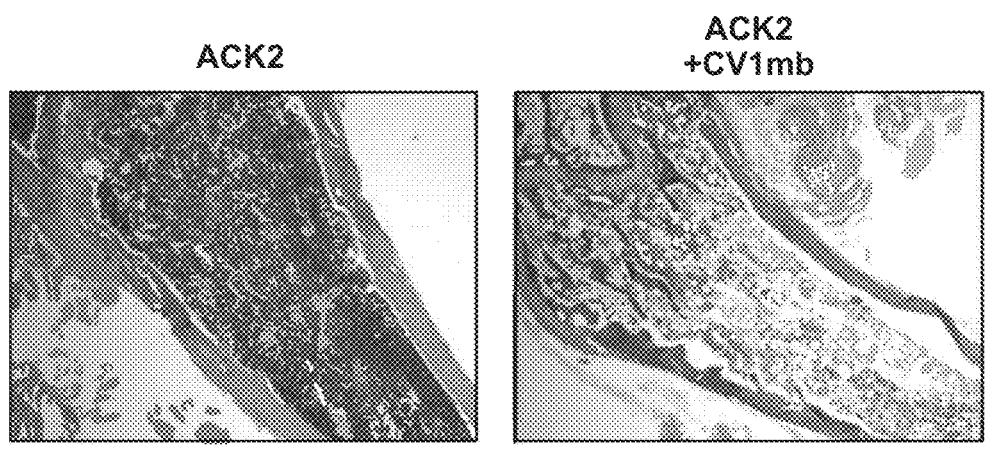
Figure 5A:
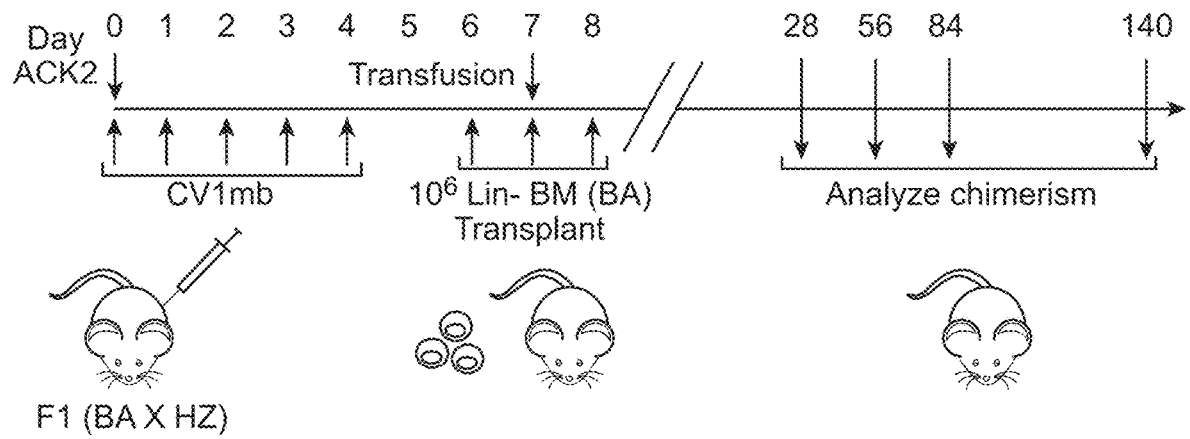
FIG. 5a-5f. Preconditioning with anti-c-Kit and CD47 blockade enables long-term engraftment of HSCs in immunocompetent mice.
Figure 5B:
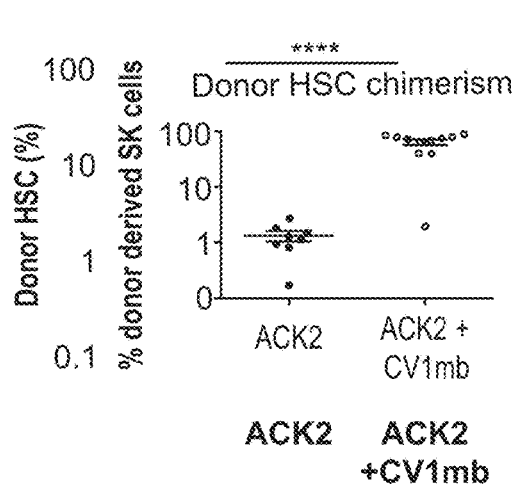
Figure 5C:
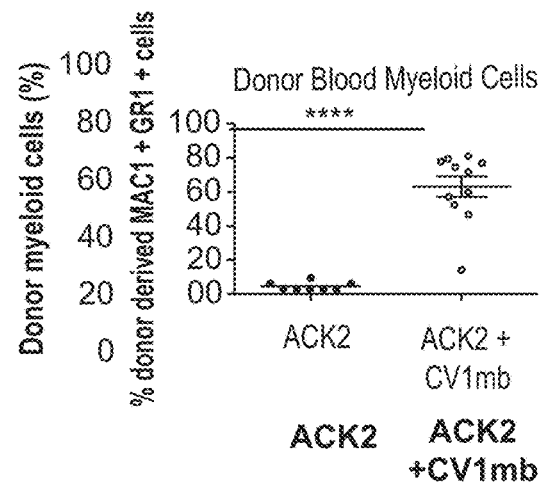
Figure 5D:
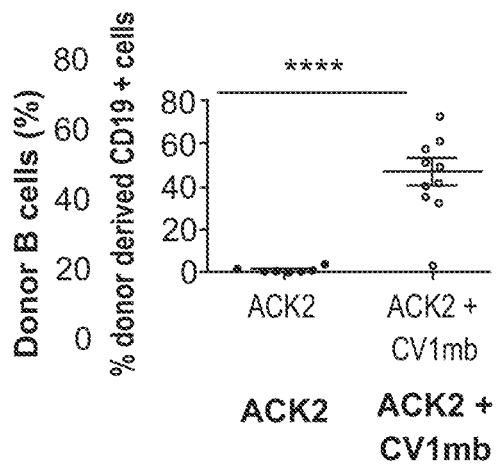
Figure 5E:
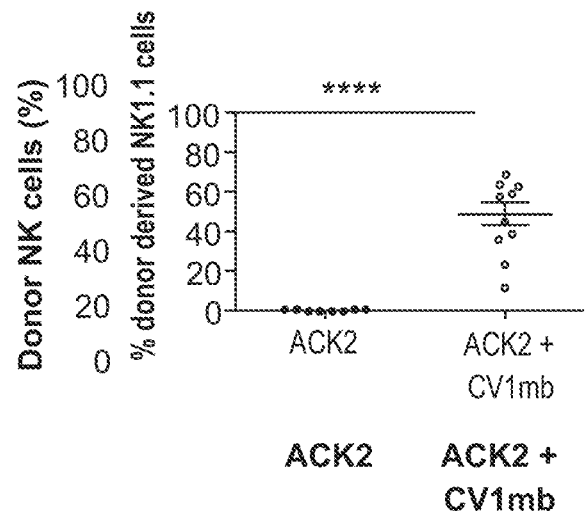
Figure 5F:
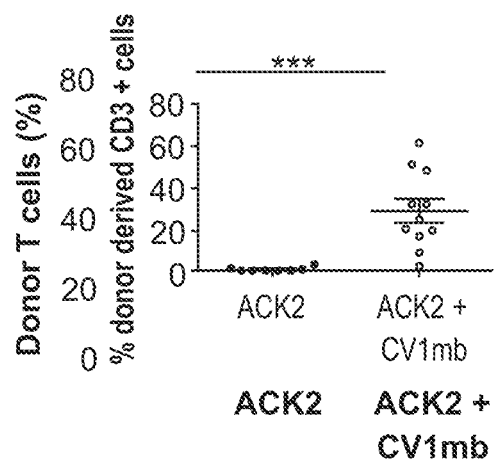

To assess the presence of functional HSCs in these mice, we performed competitive transplantation analysis in lethally-irradiated recipients. Equal numbers of whole bone marrow cells from Fc receptor-deficient mice which had been treated with and without ACK2 treatment were co-transplanted with support whole bone marrow from a mouse expressing a different CD45 allele to ensure host survival. Recipients were lethally irradiated and the source of hematopoietic cells was determined based on CD45 allele type. At 18 weeks post-transplant no significant difference in Lin$^-$Sca-1$^+$c-Kit$^+$ (LSK) hematopoietic stem and progenitor cell (HSPC) chimerism was observed between recipients that received bone marrow from ACK2-treated or untreated Fc receptor deficient mice (FIG. 4d). Taken together, the results of these studies using ACK2 Fab fragments and Fc receptor knockout mice establish that antibody Fc effector functions elicited by ACK2 are necessary for its in vivo HSC depletive activity.

CD47, a transmembrane protein expressed on HSC and many other cell types, is a 'don't eat me' signal that is an innate immune checkpoint, and acts as a critical "marker of self" to attenuate antibody dependent cell-mediated cytotoxicity/phagocytosis (ADCC/ADCP) via its interaction with SIRPα on neutrophils and macrophages. Mobilized or naturally circulating HSCs in the periphery upregulate expression of surface CD47 to avoid destruction by macrophages in the perisinusoidal spaces in bone marrow, spleen, and liver. High levels of CD47 expression on many different cancer cells similarly confers protection of cancer cells from phagocytosis. Blockade of the CD47:SIRPα axis dramatically enhances the ADC activity of tumor-opsonizing monoclonal antibodies in vitro and in vivo. We thus hypothesized that interruption of the CD47:SIRPα interaction might similarly enhance depletion of endogenous HSCs using ACK2 or other anti-c-Kit antibodies.

Figure 3A:
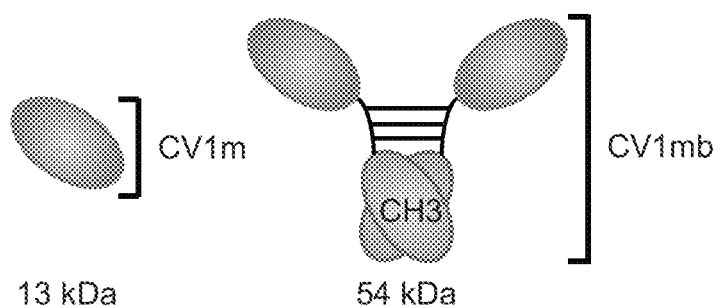
FIG. 3a-3b. Engineering a CV1 'microbody' (CV1mb) as an antagonist of murine CD47.

CD47 blockade augments the efficacy of ACK2 for transplant conditioning. We previously engineered fragments of human SIRPα as high-affinity antagonists of CD47. The most potent of these variants, CV1 (consensus variant 1), binds human CD47 (hCD47) with an affinity of 11 pM, but cross-reacts weakly with mouse CD47 (mCD47) with >1000-fold lower affinity than hCD47. We thus sought to redesign CV1 as an antagonist of mCD47 by fusing CV1 to the CH3 domain of human IgG1 through a disulfide-containing hinge (FIG. 3a). We reasoned that this new molecule, which we termed a CV1 "microbody" (CV1mb), would have enhanced affinity for mCD47 owing to the avidity afforded by its dimeric architecture.

Figure 3B:
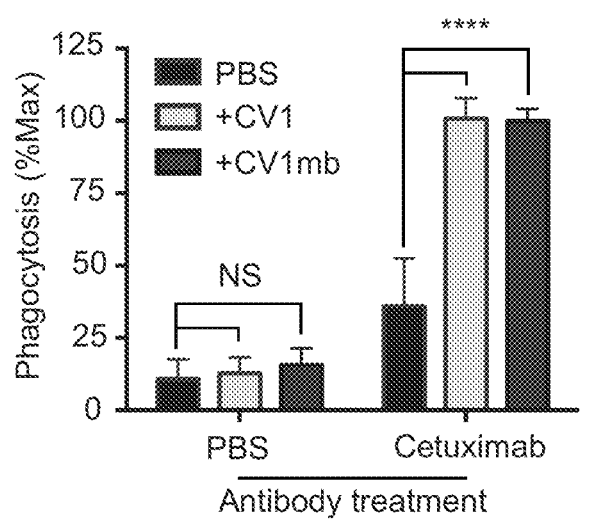

In vitro, CV1mb was functionally equivalent to monomeric CV1, as it induced no phagocytosis by itself but robustly synergized with an opsonizing monoclonal antibody, cetuximab, which binds to the epidermal growth factor receptor (EGFR) present on a colon cancer cell line (FIG. 3b). Thus, the favorable binding, functional, and pharmacokinetic properties of CV1mb indicated that it could effectively antagonize mCD47 in vivo.

We then studied the effect of combining CD47 blockade using CV1mb with ACK2 treatment in fully immunocompetent C57BL/6.CD90.1 (BA) animals. As seen previously, administration of 500 µg ACK2 alone in BA mice did not produce a sustained reduction of immunophenotypic HSCs after seven days. Similarly, daily intraperitoneal (IP) injections for five days with 500 µg CV1mb alone had no appreciable effect on immunophenotypic HSC numbers at the same time point. However, the combination of ACK2 and CV1mb resulted in a dramatic (>10,000 fold) reduction of LSK CD150+Flt3−CD34− LT-HSCs as determined by flow cytometric analysis.

Figure 6A:
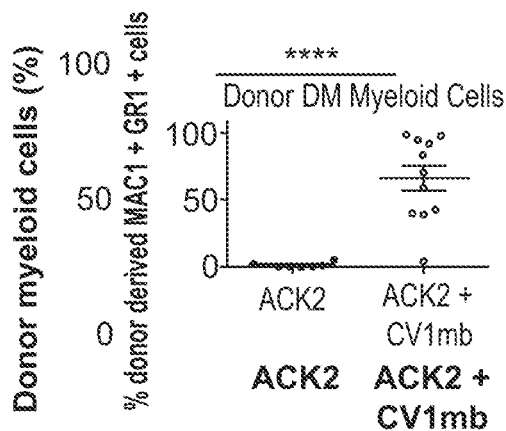
FIG. 6a-6i. Preconditioning with anti-c-Kit and CV1mb enables long-term multilineage hematopoietic engraftment in immunocompetent mice 20 weeks post transplantation. Donor chimerism of Gr-1+Mac-1+ granulocytes in (FIG. 6a), bone marrow and (FIG. 6e), spleen.
Figure 6B:
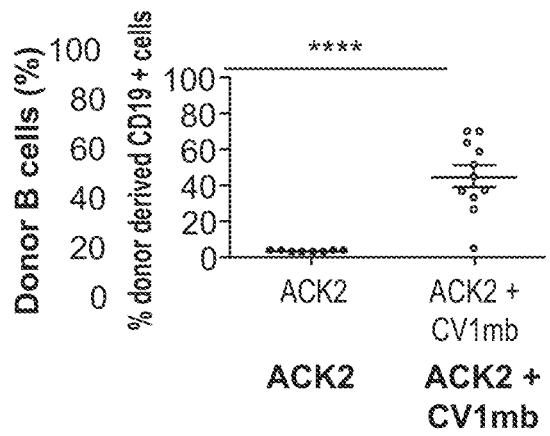
Figure 6C:
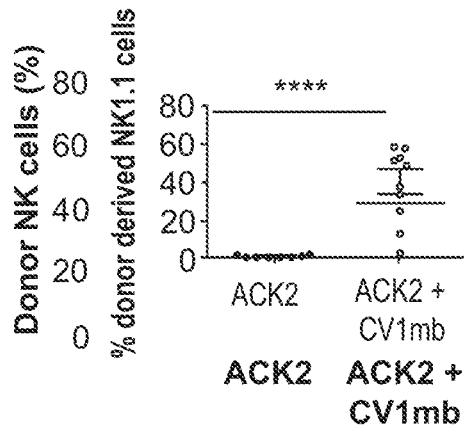
Figure 6D:
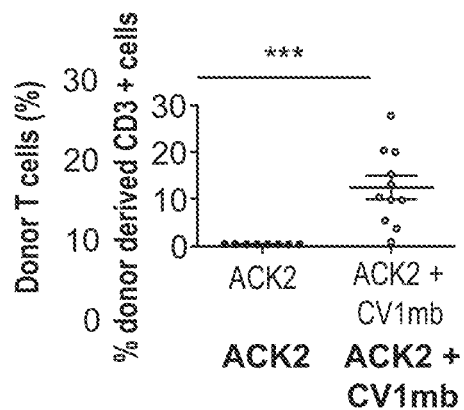
Figure 6E:
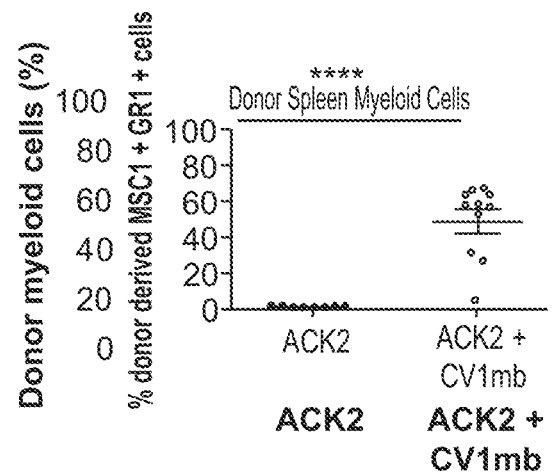
Figure 6F:
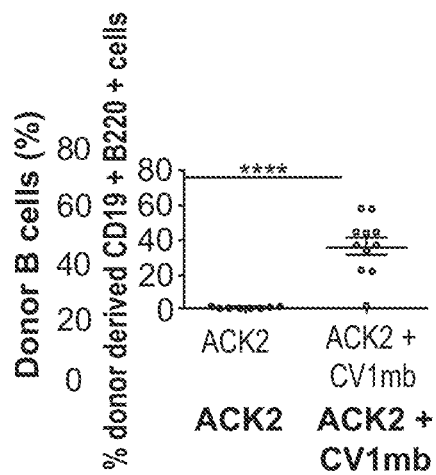
Figure 6G:
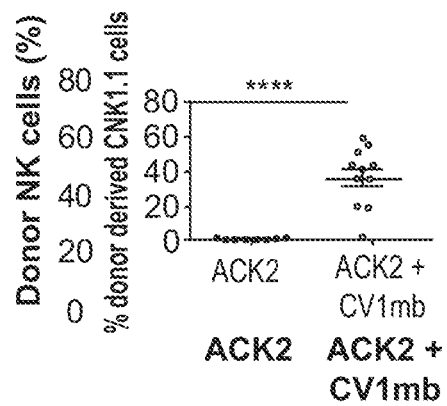
Figure 6H:
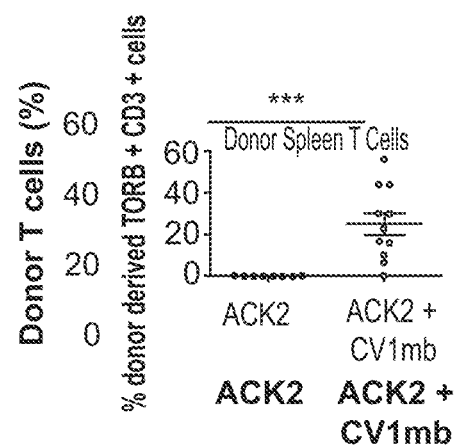
Figure 6I:
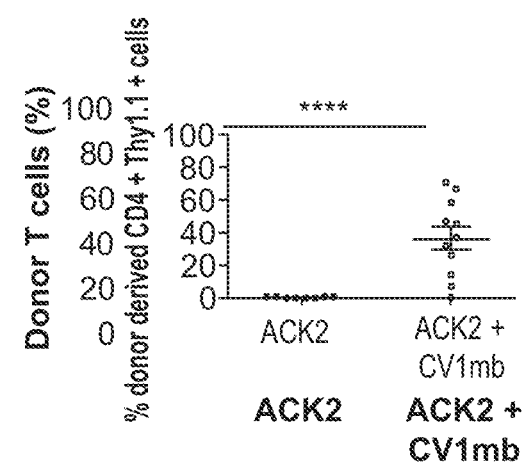
Figure 7A:
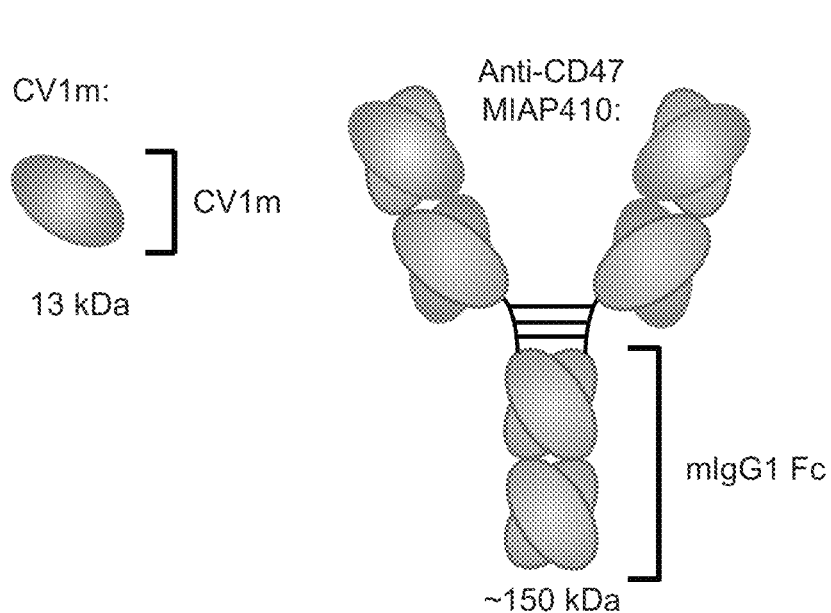
FIG. 7a-7b. Treatment with anti-c-Kit antibody ACK2 combined with CD47 blocking reagents depletes functional HSCs (FIG. 7a), Schematic of CD47-targeting reagents.
Figure 7B:
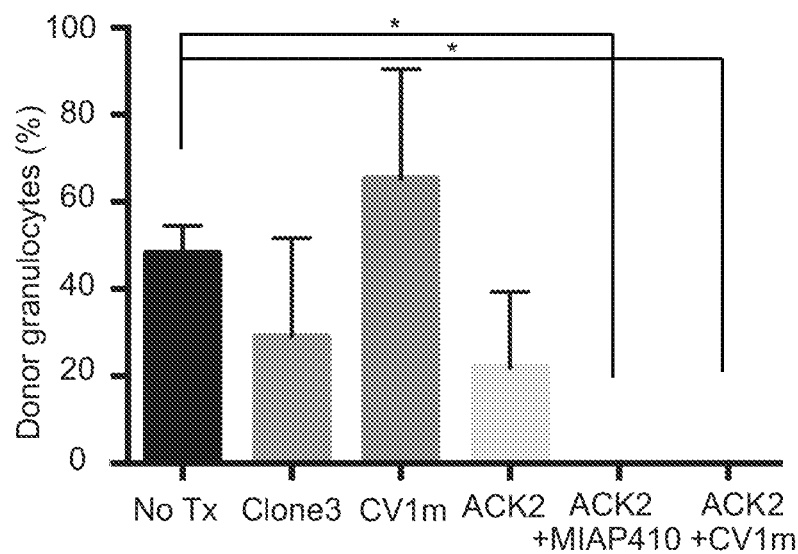
Figure 8A:
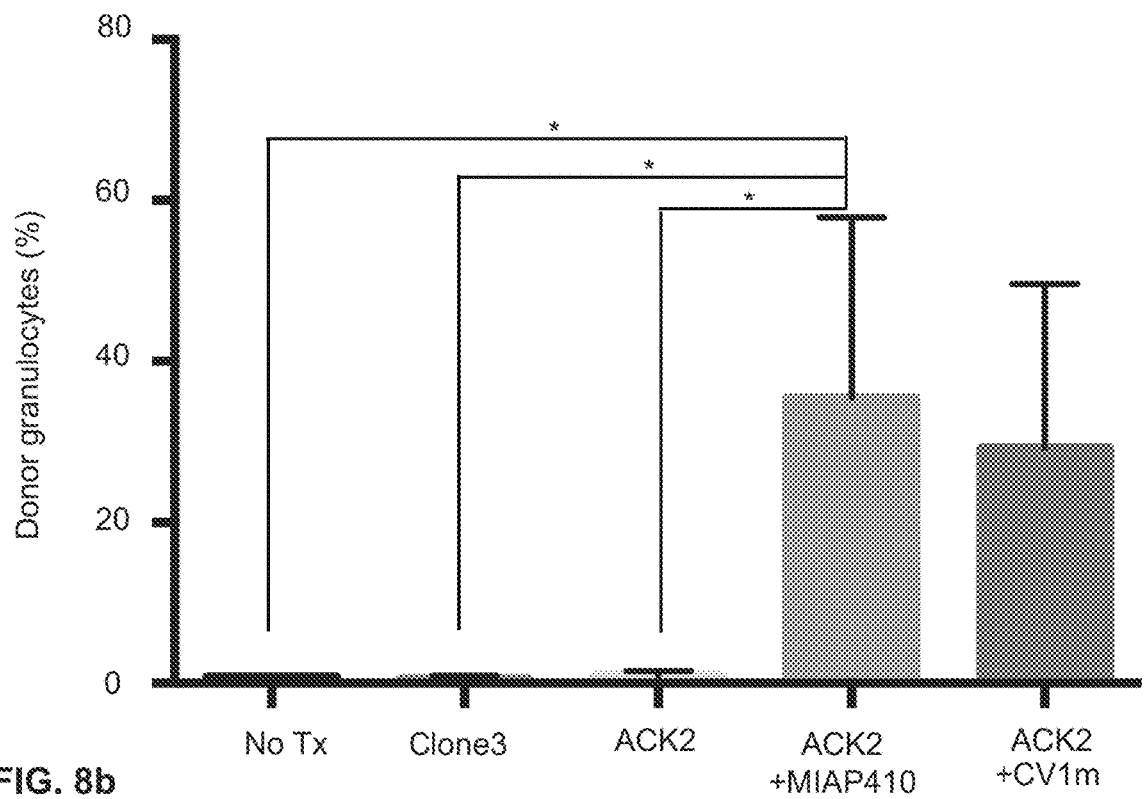
FIG. 8a-8b. Anti-c-Kit antibody ACK2 combined with CD47 blocking reagents enables granulocyte chimerism in immunocompetent recipients. Frequency of donor derived (FIG. 8a), Mac-1+Gr-1+ granulocytes and (FIG. 8b), CD19+ B cells in the peripheral blood 8 weeks after transplant in recipients treated with ACK2 and the indicated CD47-targeting reagents as compared to untreated mice (mean±s.e.m. * p<0.05, n=3-5).

To confirm that functional HSCs were indeed eliminated, whole bone marrow from ACK2/CV1mb-treated mice was co-transplanted with an equal number of GFP+ bone marrow cells from unmanipulated mice into lethally-irradiated recipients. HSC chimerism measured at 24 weeks post-transplant was significantly reduced in recipients transplanted with bone marrow from ACK2 plus CV1mb-treated mice. In contrast, robust donor chimerism was observed in recipients of marrow from untreated and ACK2-treated mice (FIG. 6b). As c-Kit is expressed in the hematopoietic progenitor cells downstream of HSC (FIG. 8a), we hypothesized that these populations might also be targeted by ACK2 combined with CV1mb. A significant loss of all downstream myeloid progenitors was observed in mice treated with the combination of ACK2 and CV1mb (FIG. 6c). Accordingly, mice treated with combined ACK2 and CV1mb developed severe anemia with reduction of hematocrit, red blood cells and hemoglobin, as well as a decrease in white blood cells (FIG. 6d). By histological examination, administration of ACK2 with CV1mb caused marked reduction of bone marrow cellularity. The clearance of the bone marrow by 7 days post-treatment was characterized by a dramatic loss of mononuclear cells and red blood cells revealing marrow adipocytes. Thus, the near complete depletion of HSCs and hematopoietic precursor cells, and the apparent clearance of the bone marrow niche space by ACK2 plus CV1mb indicated that this combination could effectively precondition WT mice for HSC transplantation.

Preconditioning with ACK2 and CD47 blockade enables HSC transplantation in WT mice. To assess whether the combination of anti-c-Kit and CD47 blockade could permit donor HSC engraftment in the absence of chemotherapy or radiation, we treated fully immunocompetent CD45.1/CD45.2 adult mice with a single dose of 500 µg ACK2 and five daily injections of 500 µg CV1mb. Severely anemic mice were given blood transfusions to ensure survival. Starting on day 6 post-treatment, lineage-depleted CD45.2+ bone marrow cells were transplanted daily for 3 consecutive days. While mice treated with ACK2 alone had very low levels of HSC engraftment, mice receiving the combination of ACK2 and CV1mb exhibited high levels of HSC engraftment 20 weeks post-transplantation, approximately two orders of magnitude greater than the antibody alone. Over 60% donor-derived granulocytes cells were observed in peripheral blood of ACK2 and CV1mb treated mice as well as in bone marrow and spleen. The engraftment was not limited to the myeloid compartment as we observed 40-50% B cell, approximately 30% T cell and around 60% natural killer cell engraftment in blood, as well as the spleen and bone marrow. T cell engraftment was also observed in the thymus, consistent with the expression of c-kit on the earliest functional pre-T cells in the thymus.

Figure 10:
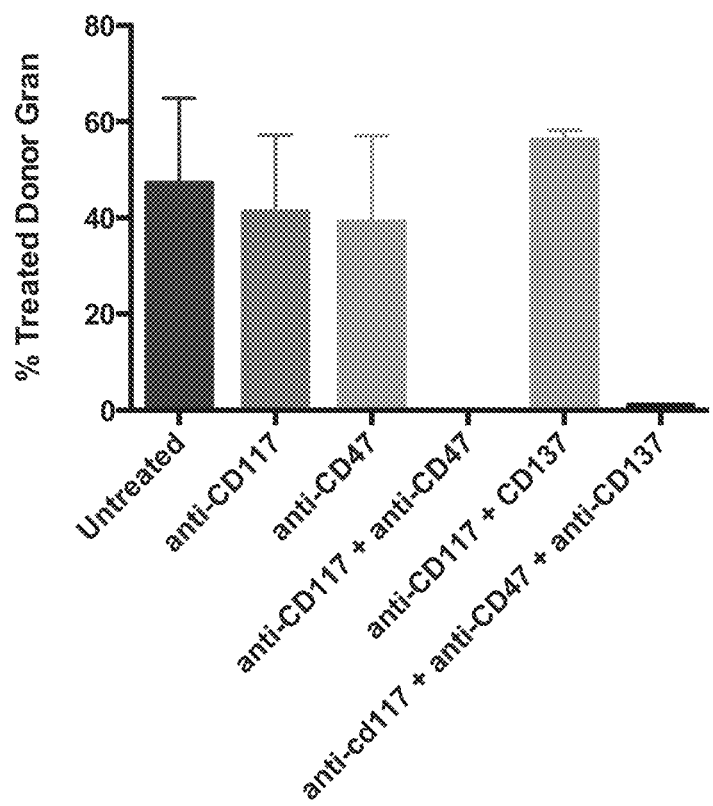
FIG. 10. Treated BA (CD45.2) donor granulocyte chimerism in lethally irradiated F1 (CD45.1×CD45.2) BA mice (CD45.2) were treated with anti-c-Kit ACK2 and anti-CD47 (MIAP410) as well as anti-CD137. On day six of the treatment regimen, these mice were sacrificed and whole bone marrow cells were isolated from their femurs. $1 \times 10^6$ whole bone marrow cells from treated mice were cotransplanted with $1 \times 10^6$ whole bone marrow cells isolated from untreated HZ mice (CD45.1) into lethally irradiated host F1 (CD45.1×CD45.2) mice. Donor granulocyte chimerism was assessed at four weeks post transplant. Both the anti-CD47+ anti-CD117 treated and the triple therapy (anti-CD137+anti-CD47+anti-CD117) show essentially minimal/no BA (CD45.2) donor granulocyte chimerism implying profound depletion of hematopoietic stem cells in the initially treated BA animals.
Figure 11A:
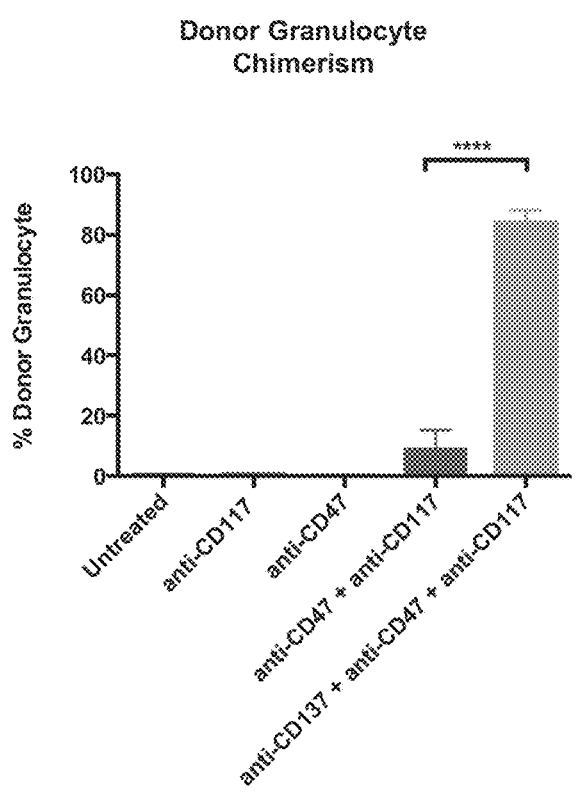
FIG. 11a-11b.
Figure 11B:
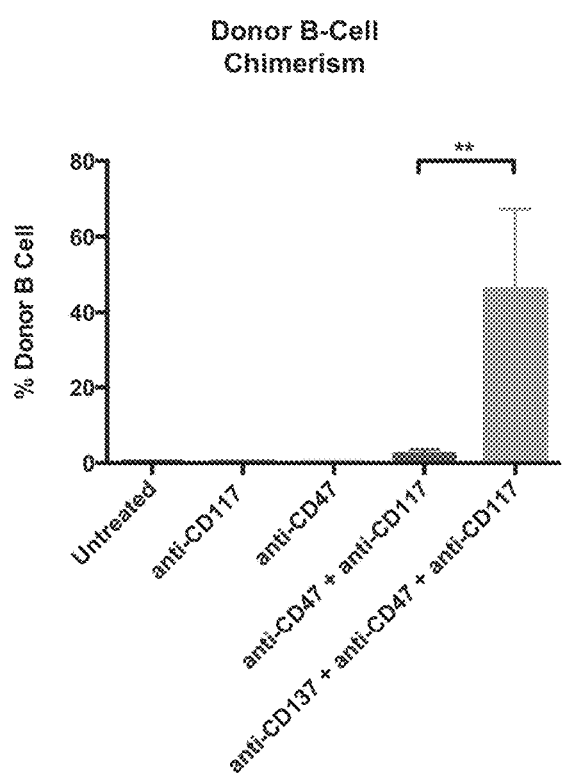

Given the robust synergism between ACK2 and CV1mb, we sought to determine if conditioning with ACK2 could be generalized to other CD47 antagonists. We thus administered ACK2 with monomeric CV1 (CV1) and an anti-CD47 antibody that blocks both mouse and human CD47 (MIAP410; FIG. 10). These combinations effectively enhanced ACK2-mediated depletion of functional HSCs, as determined by a competition transplant assay. Furthermore, CV1 and MIAP410 enabled HSC transplantation when combined with ACK2 for conditioning, yielding 29% and 35% granulocyte chimerism respectively (FIG. 11a). However, B cell chimerism remained low, with CV1 and ACK2 yielding 1.5% and MIAP410 combined with ACK2 resulting in 7% donor B cells (FIG. 11b). These results indicate that pharmacologic CD47 blockade acts to potentiate the HSC-depletive activity of anti-c-Kit antibodies, and that the magnitude of the effect is influenced by the size, affinity/avidity, and/or antibody isotype of the CD47 antagonist.

A principal limitation of hematopoietic stem cell transplantation remains the safe and facile liberation of the niche space to accept the donor graft. Our results establish that treatment of adult immunocompetent mice with two biologic agents, opsonizing anti-c-Kit antibodies and a CD47 antagonist, leads to the extensive depletion of HSC and progenitor cells, and enables exogenous HSCs to robustly engraft. This approach can obviate the need for non-specific toxic therapies which are the current standard. The development of safer and better-tolerated conditioning will allow for HSC transplantation to be extended to a broader set of patients. This prospect is particularly appealing in the era of modern gene-editing technologies, and it is readily conceivable that an anti-c-Kit plus CV1mb or anti-CD47 antibody such as Hu5F9G426 regimen could enable autologous gene-edited HSC transplants to effectively cure inherited immunodeficiency, inborn errors of metabolism, and other diseases. Additionally, by depleting HSCs and the erythroid lineage, such conditioning could prove beneficial for treating patients with hemoglobinopathies who are known to be highly resistant to hematopoietic engraftment when given conventional regimens.

Extension of this approach to allotransplantation of HSC may utilize synergy of anti-CD47 reagents with anti-T cell, and for haplo-HLA transplants anti-NK antibodies to eliminate the host immune barriers to transplantation, along with the anti-c-kit antibodies to provide functional niche space for donor HSC. Finally, these results suggest a wide therapeutic application for blockade of the CD47/SIRPα pathway. Thus far, CD47 blockade has largely been applied to directing myeloid effector responses against cancers. The robust synergism between pharmacologic CD47 antagonism and anti-c-Kit antibodies shown here in a fully syngeneic model provides strong evidence for the value of using CD47 blockade to increase the cell depletive capacity of therapeutic antibodies that target non-malignant cells. The compelling therapeutic profile that anti-c-Kit antibodies combined with CD47 antagonism exhibited in allowing robust HSC engraftment suggests that such targeted therapy may soon supplant the toxic therapies that have been used for decades to achieve HSC replacement in patients with non-malignant disorders correctable with HCT or HSC transplants.

Methods

Protein expression and purification. CV-1 was expressed and purified from BL21(DE3) E. coli cells as previously described. For production of CV1mb, the CV1mb coding sequence was cloned in-frame with an N-terminal GP67 leader sequence and C-terminal 8× histidine tag into the baculovirus expression vector pAcGP67. Recombinant CV1mb baculovirus was prepared in Sf9 cells and CV1mb protein expressed by infection of Hi5 cells. 60 hours postinfection, secreted CV1mb was purified from the culture medium by Ni-NTA chromatography. Endotoxin was removed by column washes with Triton X-114 as previously described. Purified proteins were desalted into phosphate buffered saline (PBS) and passed through a sterile 0.22 µM filter.

Production and purification of ACK2 F[ab] fragments. Intact ACK2 antibody was digested using immobilized papain (Thermo) according to the manufacturer's instructions. Undigested ACK2 and Fc products were removed by passage of the reaction mixture over a protein A column, followed by ion exchange chromatography with a monoQ column. Purified Fab fragments were desalted into PBS and filtered with a 0.22 µM filter.

Mice. Mice used were 8-12 weeks old congenically distinguishable CD45.1, CD45.2 or CD45.1/CD45.2 C57Bl/Ka or C57Bl/Ka.CD90.1 mice, $Rag2^{-/-}c\gamma^{-/-}$ mice or $Fcer1g^{-/-}$ mice. All procedures were approved by the International Animal Care and Use Committee. Mouse strains were bred and maintained at Stanford University's Research Animal Facility.

Phagocytosis assays. Human macrophages were obtained by differentiation of human peripheral blood monocytes and phagocytosis with GFP+ DLD-1 colon cancer cells was performed as previously described. Briefly, 50,000 macrophages and 100,000 GFP+ DLD-1 cells were co-cultured per well of a 96-well plate and incubated with the given treatments in serum-free IMDM at 37° C. for two hours. The cell mixtures were then washed with autoMACS Running Buffer (Miltenyi) and stained with anti-CD45 (BioLegend) to label macrophages and DAPI (Sigma) to assess cell viability. Phagocytosis was determined by flow cytometry as the percentage of GFP+ macrophages (CD45+ cells) with an LSRFortessa. Flow cytometry data was analyzed using FlowJo and plotted in Prism 6 after normalization as the percentage of maximal phagocytosis. Statistical significance was determined in Prism by two-way ANOVA with correction for multiple comparisons.

Complete blood count analysis. 20 µl of whole blood per mouse was collected via the tail vein. Complete blood counts were conducted using Heska Hematrue Vetarinary Hematology Analyzer.

Peripheral blood cell preparation for flow cytometry. Approximately 100 µl of whole blood was collected via the tail vein. Blood was incubated on 2% dextran in PBS for 45 minutes at 37° C. Supernatant was extracted and lysed in ACK lysis buffer for 7 minutes on ice.

Bone marrow cell preparation. Mice were euthanized and femurs and tibias were collected. Bones were crushed in PBS supplemented with 2% heat-inactivated FBS. Cells were filtered through a 70-µm filter (Falcon). Bone marrow cells were lysed in ACK lysis buffer for 7 minutes on ice. Cells were filtered through a 70-µm filter (Falcon) and then counted on a Countess automated cell counter (Invitrogen).

Lineage negative cell isolation from bone marrow for transplant. Mice were euthanized and femurs, tibias, humeri and coxa bones were collected. Bones were crushed in PBS supplemented with 2% heat-inactivated FBS. Cells were filtered through a 70-µm filter (Falcon). Bone marrow cells were lysed in ACK lysis buffer for 7 minutes on ice. Cells were filtered through a 70-µm filter (Falcon) and then counted on a Countess automated cell counter (Invitrogen). Lineage cell depletions were performed using Miltenyi Lineage Cell Depletion Kits according to the manufacturer's instructions.

Spleen and Thymus Cell Preparation for Staining and Analysis. Spleens and thymi were directly mashed in a 70-µm filter with the plunger of a 3 ml syringe. Cells were lysed in ACK lysis buffer for 7 minutes on ice. Cells were filtered through a 70-µm filter (Falcon) and then counted on a Countess automated cell counter (Invitrogen).

Flow Cytometry. All stainings were performed in 2% FBS for 20-45 minutes on ice. Cells were stained with optimal dilutions of ebioscience antibodies. Reagents used were: Mac-1 PE-Cy7 (M1/70), Mac-1 APC-Cy5 (M1/70), Mac-1 BV421 (M1/70), Mac-1 PE (M1/70), Gr-1 PE (RB6-8C5), GR-1 FITC (RB6-8C5), GR-1 BV421 (RB6-8C5), GR-1 PE (RB6-8C5), CD19 PE (ebio103), CD3 APC-Cy7 (17A2), CD45.1 APC (A20), CD45.1 BV421 (A20), CD45.1 APC (A20), CD45.2 APC (104), CD45.2 FITC 331 (104), CD45.2 BV421 (104), B220 PE-Cy7 (RA3-6B2), B220 PE (RA3-6B2), B220 BV421 (RA3-6B2), NK1.1 FITC (PK136), Nk1.1 Pe-Cy7 (PK136), TCRβ APC (H57-597), Thy1.1 Pe-Cy7 (HISS1), CD4 PE (GK1.5), CD4 BV421 (GK1.5), CD8a PE (53-6.7), CD8a BV421 (53-6.7), SCA1 Pe-Cy7 (D7), CD117 APC-Cy7 (2B8), CD117 APC (2B8), CD150 BV421 (TC15-12 F 12.2), CD135 APC (A2F10), CD34 FITC (RAM34), CD16/32 PE (93), CD34, CD127 BV421 (A7R34), CD3 PE (17A2), CD3 BV421 (17A2), CD5 PE (53-7.3), CD5 BV421 (53-7.3), Ter119 PE (TER119), Ter119 BV421 (TER119). Propidium Iodide was used to distinguish between live/dead cells. Cells were analyzed on BD LSRII at the Stanford Shared FACS Facility. Data was analyzed using FlowJo 9.5 (Tree Star). Statistical significance was determined in Prism by two-way ANOVA with correction for multiple comparisons.

Bone Marrow Transplant. Mice were given retro-orbital injections of either lineage negative bone marrow cells or whole bone marrow for competitive transplantation assays. Cells were suspended in 100 µl PBS.

Bone Marrow Histology. Femurs were dissected and fixed in 10% buffered formalin overnight. Bones were subsequently decalcified using Immunocal a formic acid based decalcification buffer. Paraffin embedding and sectioning was performed by Histo-Tec Laboratory.

Example 2

Combination of CD47 Blockade and CD137 Agonism in Conditioning

Figure 8B:
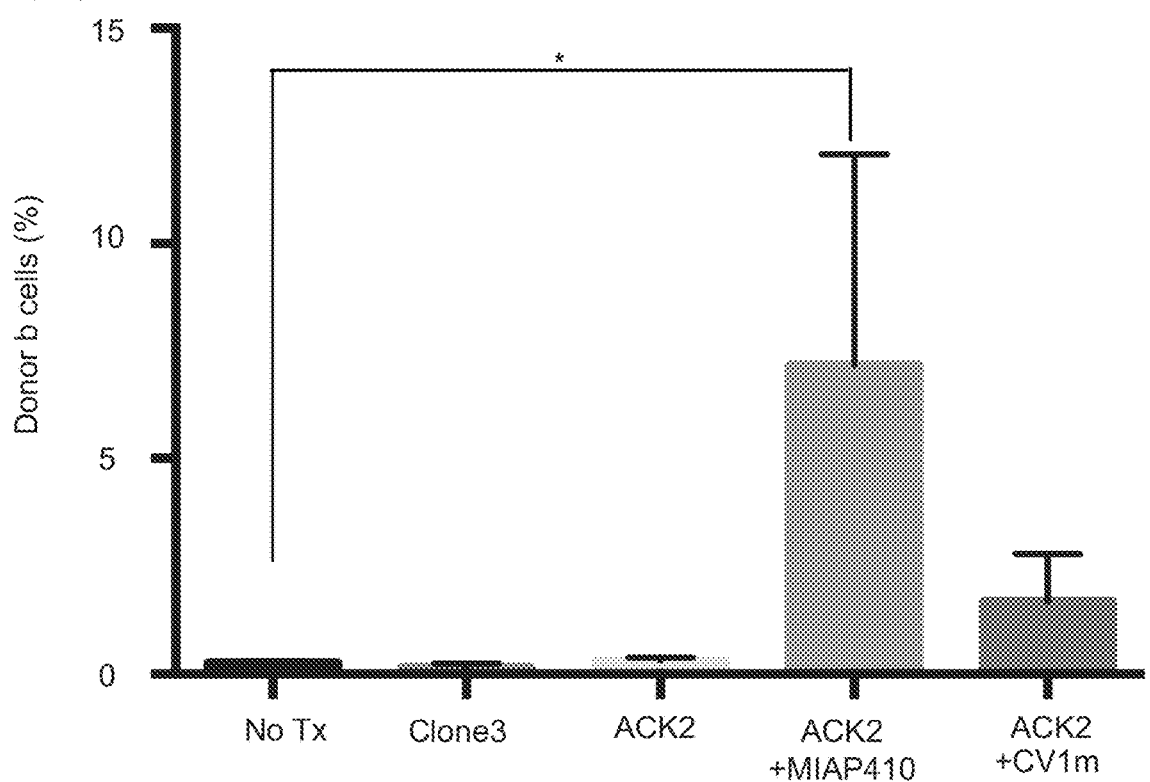
Figure 9A:
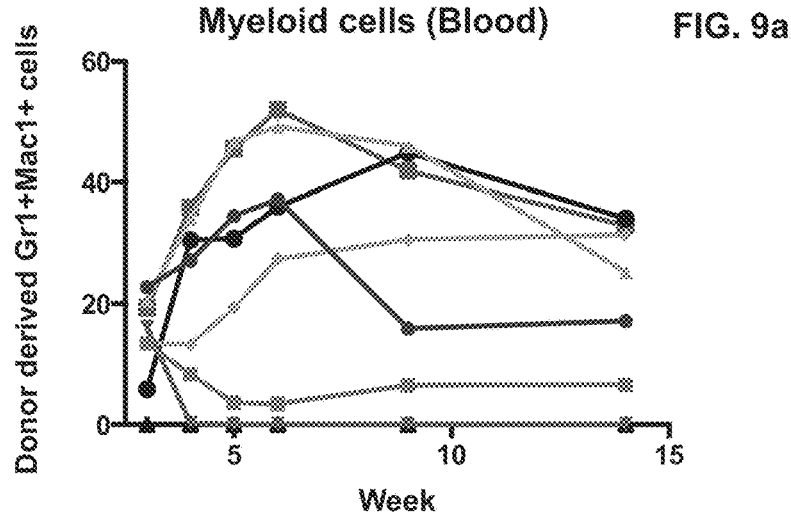
FIG. 9a-9c. Anti-c-Kit antibody ACK2 combined with anti-CD47 CV1mb, in combination with T cell depleting antibodies permits engraftment in minor MHC mismatched model of HSC transplantation. In combination with an all antibody approach (anti-CD4 and anti-CD8) for immune cell depletion our data demonstrates that this regimen can be applied in situations when there is genetic mismatch between donor and recipient.
Figure 9B:
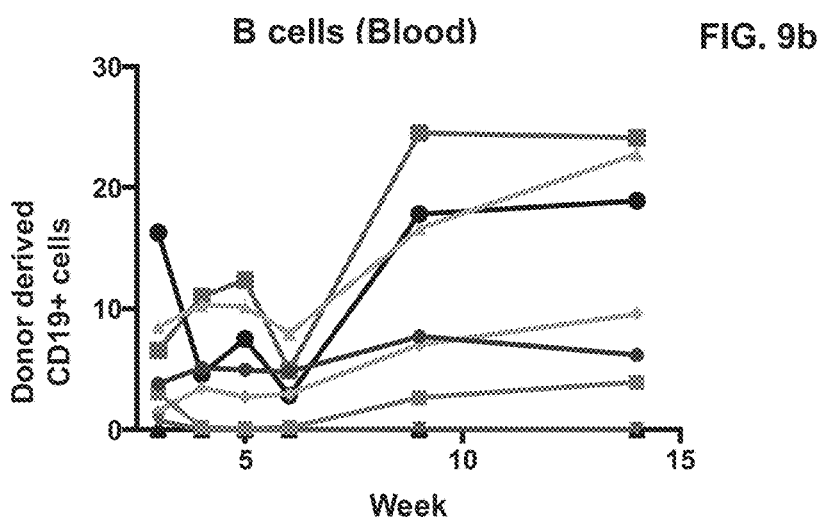
Figure 9C:
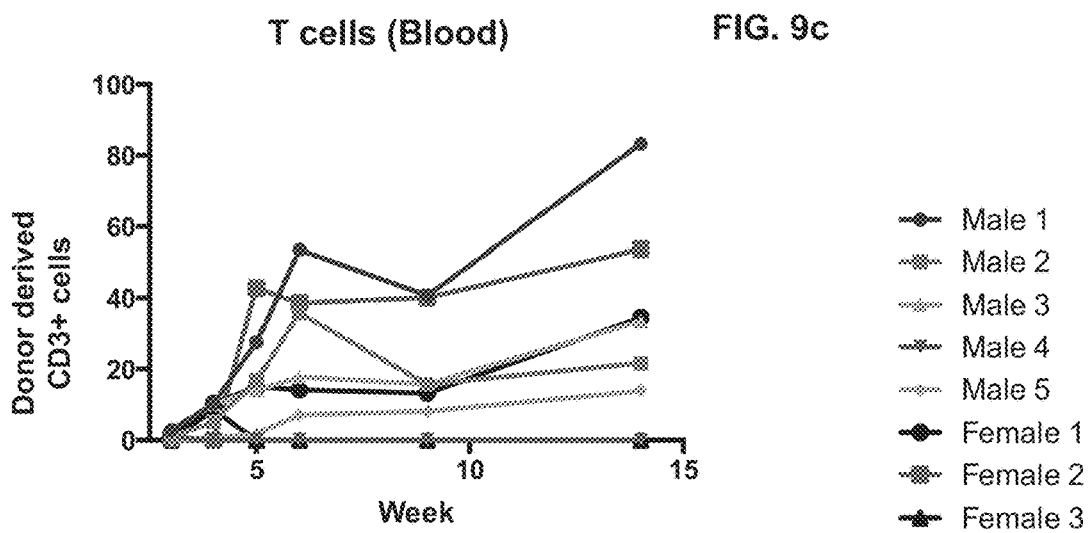

Anti-c-Kit antibody ACK2 combined with CD47 blocking reagents enables granulocyte chimerism in immunocompetent recipients. Shown in FIG. 8, the frequency of donor derived Mac-1+Gr-1+granulocytes and CD19+ B cells in the peripheral blood 8 weeks after transplant in recipients treated with ACK2 and the indicated CD47-targeting reagents as compared to untreated mice.

Figure 12A:
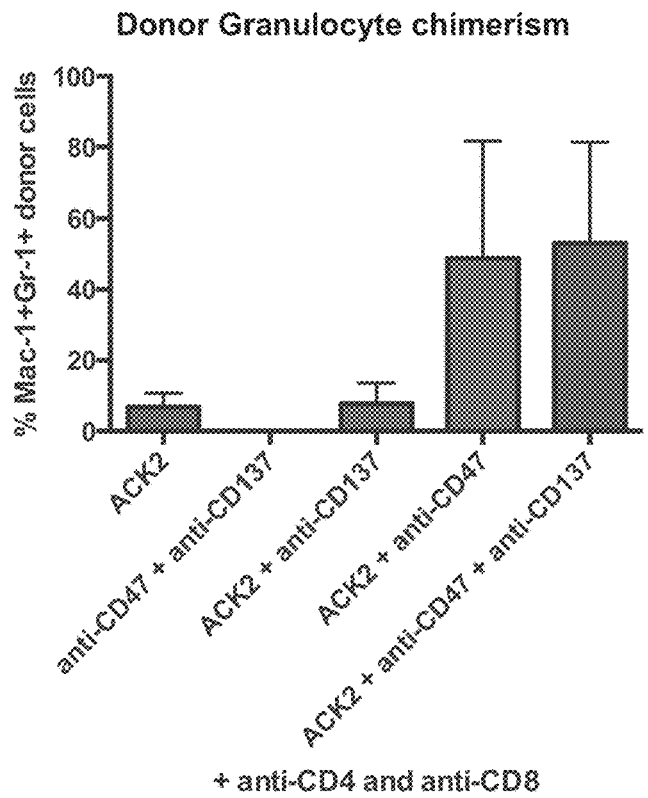
FIG. 12a-12b. Allogeneic transplantation of HSCs in a minor MHC mismatched model of transplantation using anti-c-Kit, anti-CD47 and anti-CD137 antibodies in conjunction with T cell depleting antibodies. Our data demonstrate that this triple combination regimen can be applied beyond autologous HSC transplantation to transplantation of gene-modified autologous and allogeneic of sorted HSCs. LSK HSCs were sorted from B10.D2 Donors and transplanted as per our conditioning regiment into anti-c-Kit, anti-CD47 and anti-CD137 treated Balb/C mice.
Figure 12B:
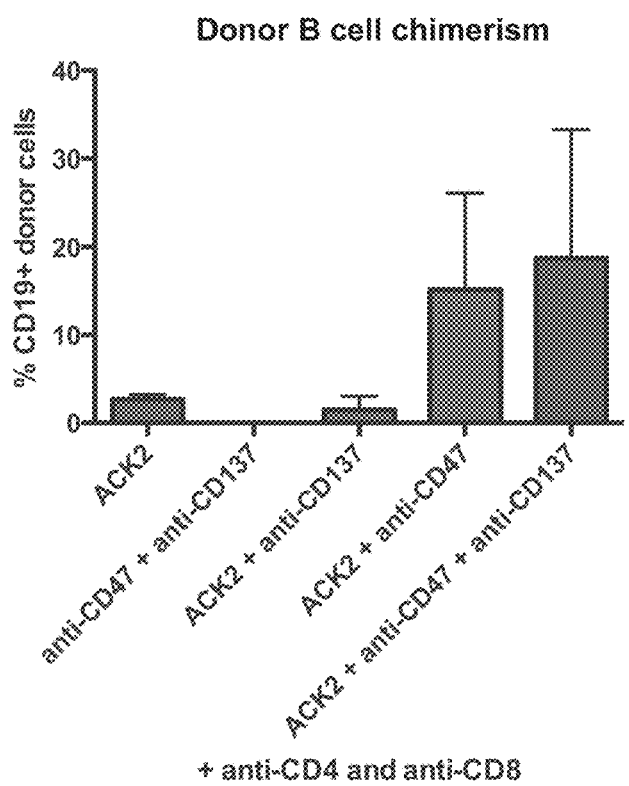

F1 mice (CD45.1×CD45.2) were treated with 500 μg of a monoclonal anti-CD117 antibody (ACK2) administered retro-orbitally in conjunction with 500 μg of a monoclonal anti-cd47 antibody (MIAP410) on Day 0. Mice were subsequently treated with 500 μg anti-CD47 (MIAP410) on Days 1, 2, 3 and 4 post initial anti-CD117 (ACK2) injection. On day 1 mice were given 500 μg of a monoclonal anti-CD137 antibody (LOB12.3), and on day 2 mice were given 100 μg of LOB12.3. On day 6, 7, and 8 mice received 1×10$^6$ lineage depleted CD45.2 bone marrow cells that are enriched for hematopoietic stem and progenitor cells. Chimerism was assessed starting at 4 weeks post transplant (FIG. 12). Mice treated with this regimen were compared to control mice that either received (i) no conditioning; (ii) anti-CD117 alone; (iii) anti-CD47 alone and (iv) anti-CD47+anti-CD117 following the same protocol.

Figure 13A:
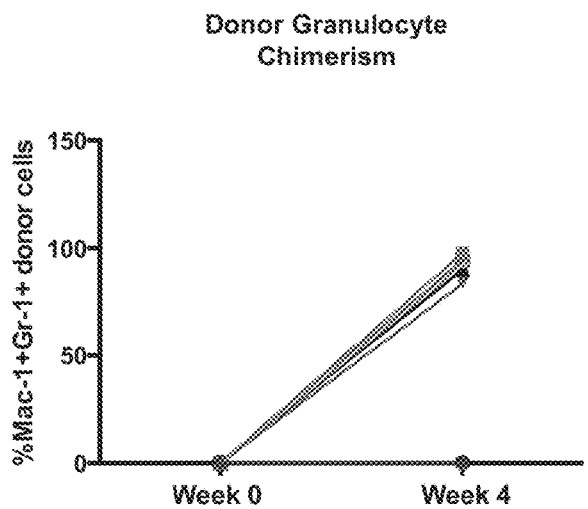
FIG. 13a-13b. Allogeneic transplantation of HSCs in a haploidentical HSC transplant model using anti-c-Kit, anti-CD47 and anti-CD137 antibodies in conjunction with T cell and NK cell depleting antibodies (anti-CD4: GK1.5, anti-CD8: yts169.4, anti-NK: asialoGM1). Our data demonstrates that this triple combination regimen can be applied beyond autologous HSC transplantation to allogeneic transplantation of sorted HSCs. LSK HSCs were sorted from B6XSJL F1 donors and transplanted as per our conditioning regiment into anti-c-Kit, anti-CD47 and anti-CD137 treated B6XBalb/C F1 mice.
Figure 13B:
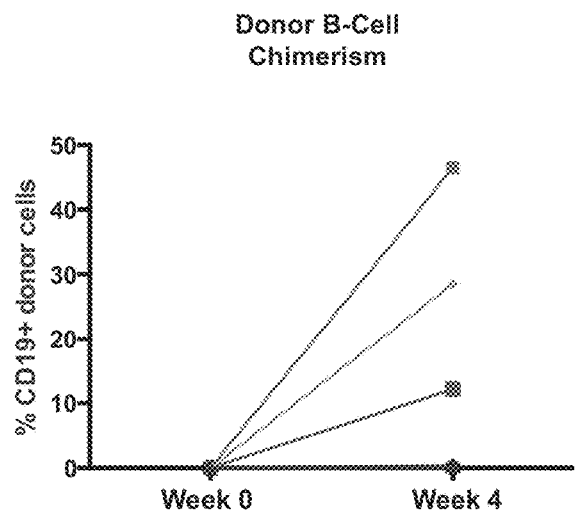

Treated BA (CD45.2) donor granulocyte chimerism in lethally irradiated F1 (CD45.1×CD45.2). BA mice (CD45.2) were treated with the regimen described above. On day six of the treatment regimen, these mice were sacrificed and whole bone marrow cells were isolated from their femurs. 1×10$^6$ whole bone marrow cells from treated mice were cotransplanted with 1×10$^6$ whole bone marrow cells isolated from untreated HZ mice (CD45.1) into lethally irradiated host F1 (CD45.1×CD45.2) mice. Donor granulocyte chimerism was assessed at four weeks post transplant. Both the anti-CD47+anti-CD117 treated and the triple therapy (anti-CD137+anti-CD47+anti-CD117) show essentially zero BA (CD45.2) donor granulocyte chimerism, implying full depletion of hematopoietic stem cells in the initially treated BA animals (FIG. 13).

Figure 14A:
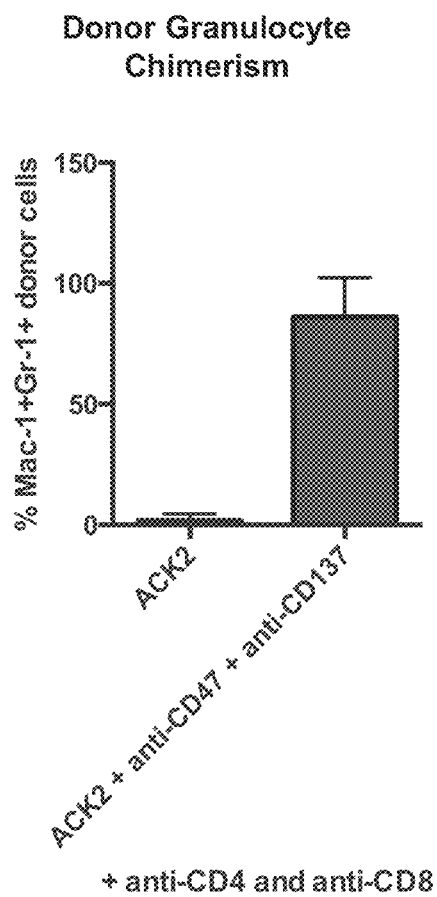
FIG. 14a-14b. Allogeneic transplantation of HSCs in a major MHC mismatch HSC transplant model using anti-c-Kit, anti-CD47 and anti-CD137 antibodies in conjunction with T cell and NK cell depleting antibodies (anti-CD4: GK1.5, anti-CD8: yts169.4, anti-NK: asialoGM1). Our data demonstrates that this triple combination regimen can be applied beyond autologous HSC transplantation to allogeneic transplantation of sorted HSCs. LSK HSCs were sorted from Akr/J donors and transplanted as per our conditioning regiment into anti-c-Kit, anti-CD47 and anti-CD137 treated HZ (C57/BL6 CD45.1 Thy1.1) mice.

BA (CD45.2) Granulocyte Chimerism in Treated F1 (CD45.2×CD45.1) animals at four weeks post transplant. F1 mice (CD45.2×CD45.1) received the indicated antibody regimens (FIG. 14A) and then received three lineage negative transplants. Donor granulocyte chimerism was measured four weeks post transplant via fluorescence-activated cell sorting. The triple therapy (anti-CD137+anti-CD47+anti-CD117) treated mice had a greater than four-fold increase in donor granulocyte chimerism relative to the mice treated with anti-CD47+anti-CD117 alone (p value<0.0001).

Figure 14B:
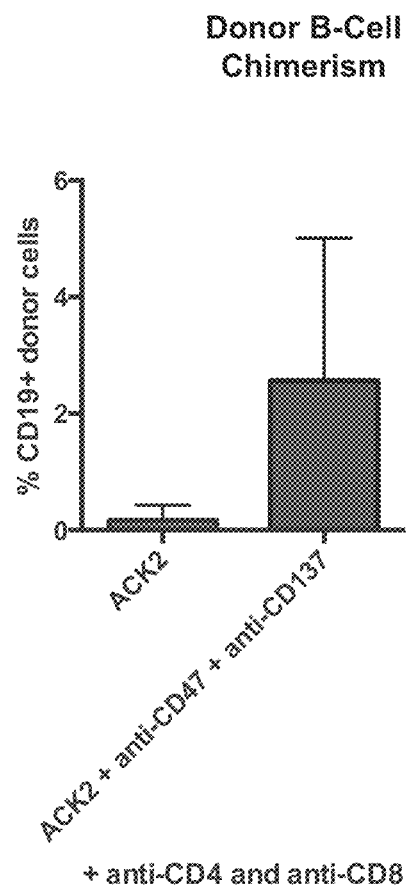

Anti-CD137 greatly increases the efficacy of anti-CD47 in the transplant setting. BA (CD45.2) B-Cell Chimerism in Treated F1 (CD45.2×CD45.1) animals at four weeks post transplant (FIG. 14B). F1 mice (CD45.2×CD45.1) received the indicated antibody regimens and then received three lineage negative transplants. Donor B-cell chimerism was measured four weeks post transplant via fluorescence-activated cell sorting. The triple therapy (anti-CD137+anti-CD47+anti-CD117) treated mice had a greater than eight-fold increase in donor B-cell chimerism relative to the mice treated with anti-CD47+anti-CD117 alone (p value=0.0028). Anti-CD137 greatly increases the efficacy of anti-CD47 in the transplant setting.

Example 3

Successful Engraftment of Hematopoietic Stem Cells into Immunocompetent Recipients Using Only Anti-CD117 Antibodies and CD47 Blockade as Conditioning Bone marrow transplantation (BMT) is an efficacious therapy for many otherwise incurable hematologic malignancies and disorders that affect production of hematopoietic cells, including life-threatening anemias, and immunodeficiency syndromes. In a successful transplantation, clearance of bone-marrow niches must be achieved for donor hematopoietic stem cell (HSC) to engraft. Current methods to clear niche space rely on radiation and/or chemotherapy, which can impart toxic adverse effects that greatly limit the potential clinical utility of BMT. Thus, there is a major clinical need for safer conditioning regimens. To this end, a monoclonal antibody against CD117 (ACK2) has been shown to transiently deplete HSCs in immunocompromised mice and enable donor cell engraftment. However, this regimen has proved ineffective in immunocompetent animals.

Figure 17:
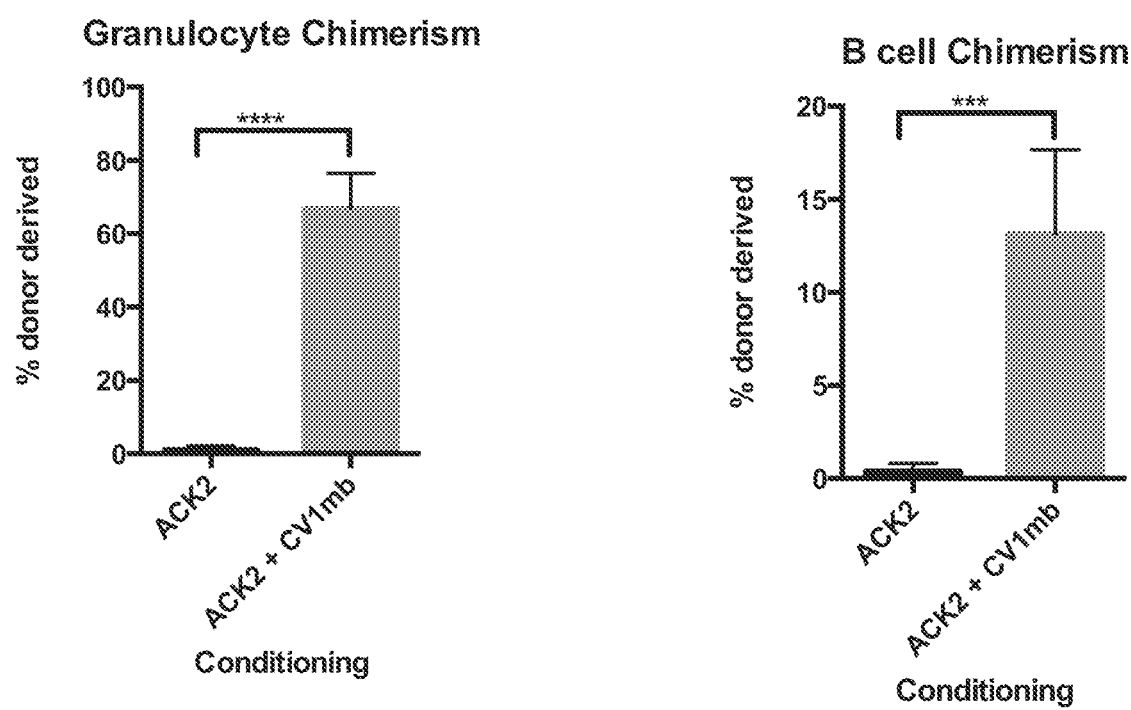
FIG. 17. High levels of chimerism is achieved in mice treated with anti-CD117 antibody and CD47 antagonist.

HSC-depletion by CD117 antibody may occur, in part, through Fc-mediated effector functions, such as antibody-dependent cellular phagocytosis (ADCP). We thus sought to enhance the ADCP activity of anti-CD117 antibodies by blocking the inhibitory CD47-SIRPα "don't eat me" pathway. Consistent with previous reports, we found treatment of wild-type mice (C57BL/6) with ACK2 alone resulted in modest and transient depletion of hematopoietic stem and progenitor cells (HSPCs). Shown in FIGS. 15-17 are the results.

Strikingly, the addition of the CD47-antagonist CV1 in combination with ACK2 resulted in rapid and prolonged depletion of bone marrow HSPCs as well as clearance of the bone marrow niche. This depletion was accompanied by profound reductions in hematocrit and blood leukocyte counts not observed in mice treated with ACK2 alone. In support of the role of Fc receptors in the treatment regimen, depletion of HSCs was not observed in mice lacking functional Fc receptors, nor in animals treated with high-doses F(ab) fragments of ACK2. Finally, high levels of granulocyte chimerism (~70%) were achieved post-BMT in mice receiving the combination of ACK2 and CV1 as compared to no chimerism in animals treated with ACK2 alone (p-value<0.0001). Our results show that targeted biologic agents have the potential to replace the toxic preconditioning therapies that are currently clinically utilized. This can lead to safer preparative regimens, which will allow BMT to treat a broader patient population and larger spectrum of hematologic disorders.

Figure 15:
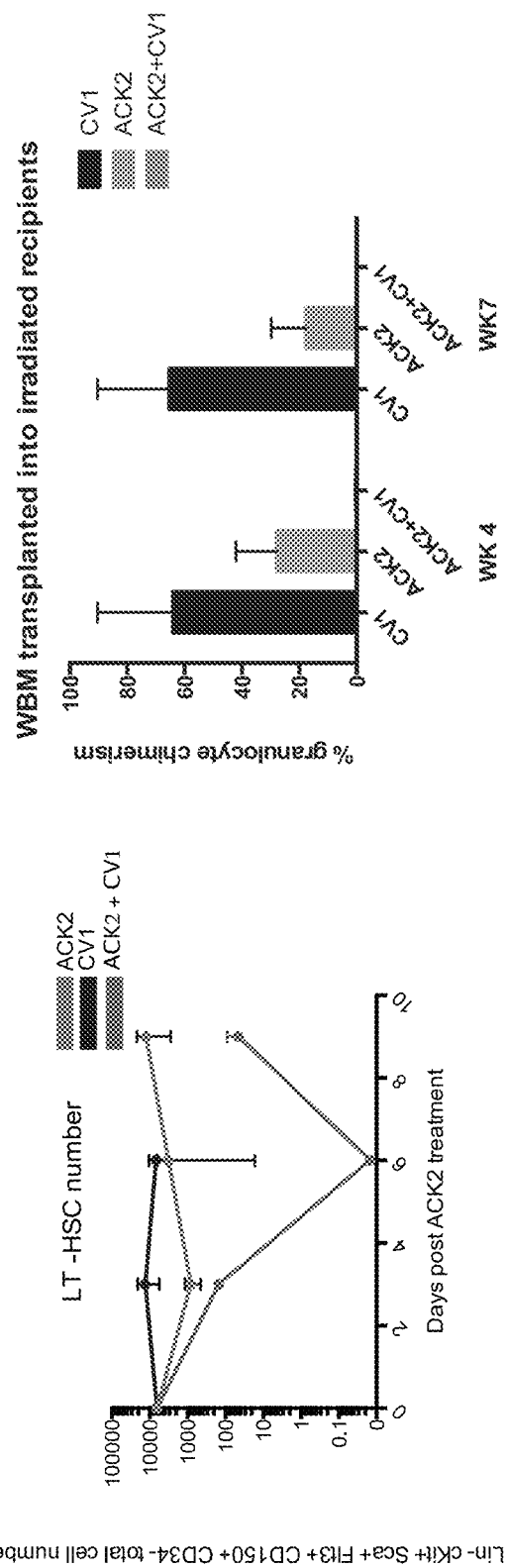
FIG. 15. High affinity SIRPα variant CV1 enhances anti-CD117 mediated HSC depletion.
Figure 16A:
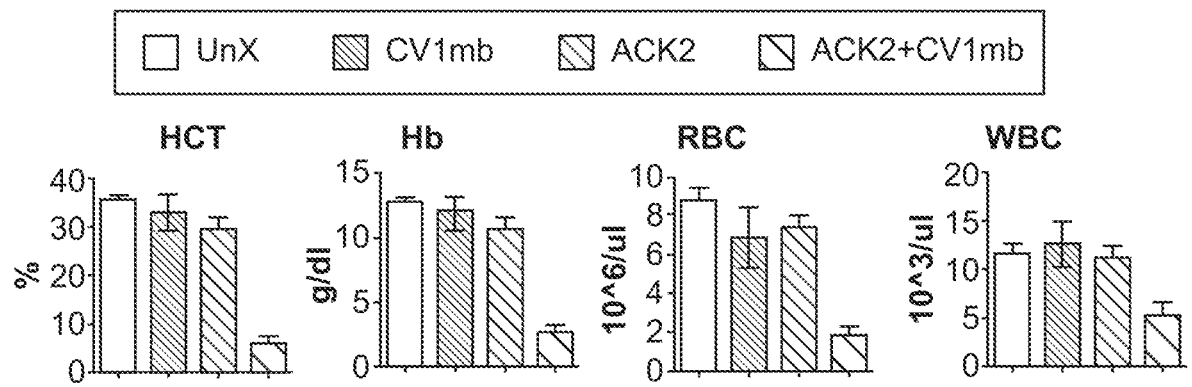
FIG. 16a-16d. High affinity SIRPα variant CV1 dimer enhances anti-CD117 mediated HSC depletion and hematopoietic cell loss.
Figure 16B:
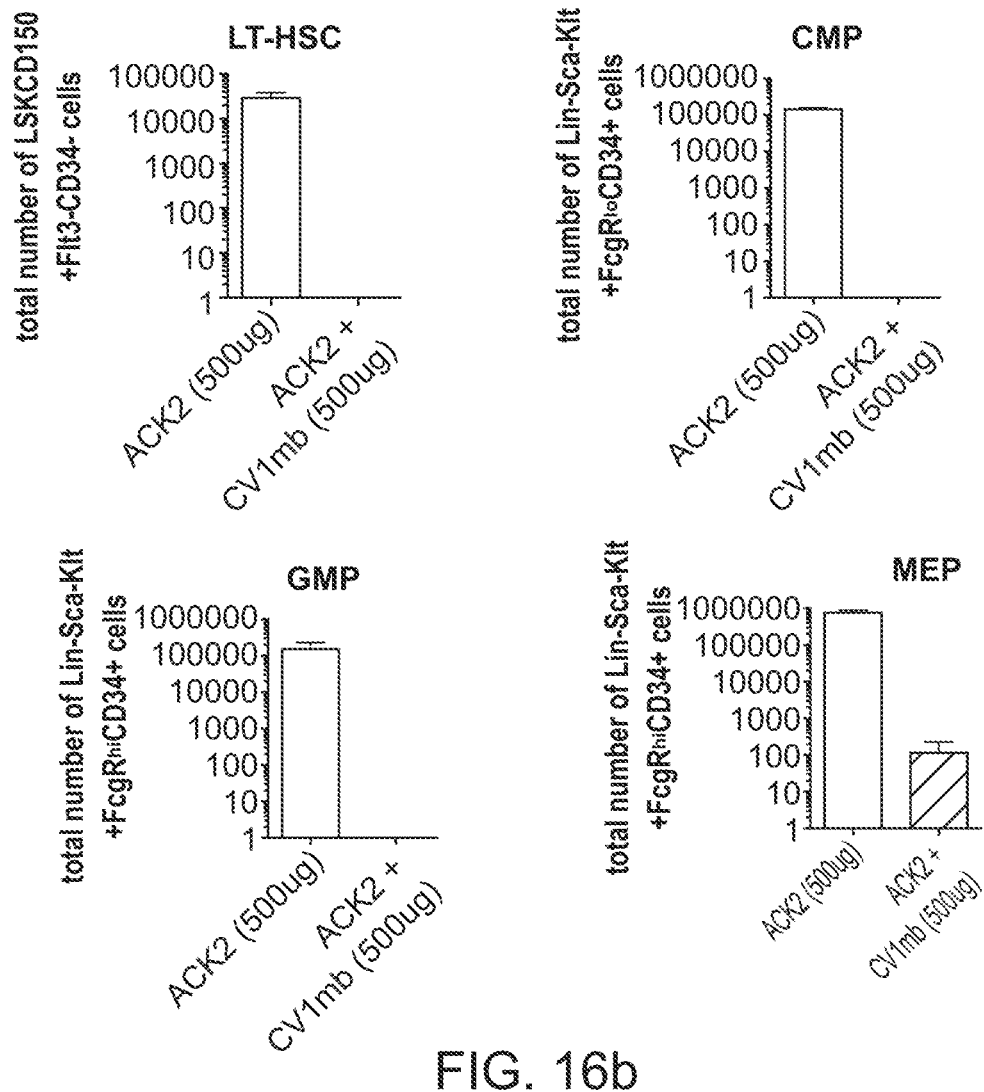
Figure 16C:
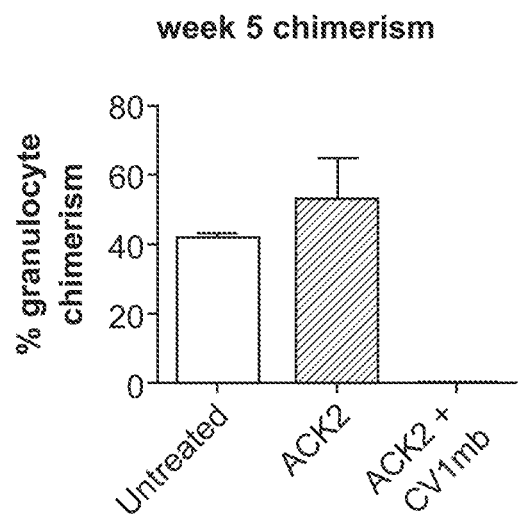
Figure 16D:
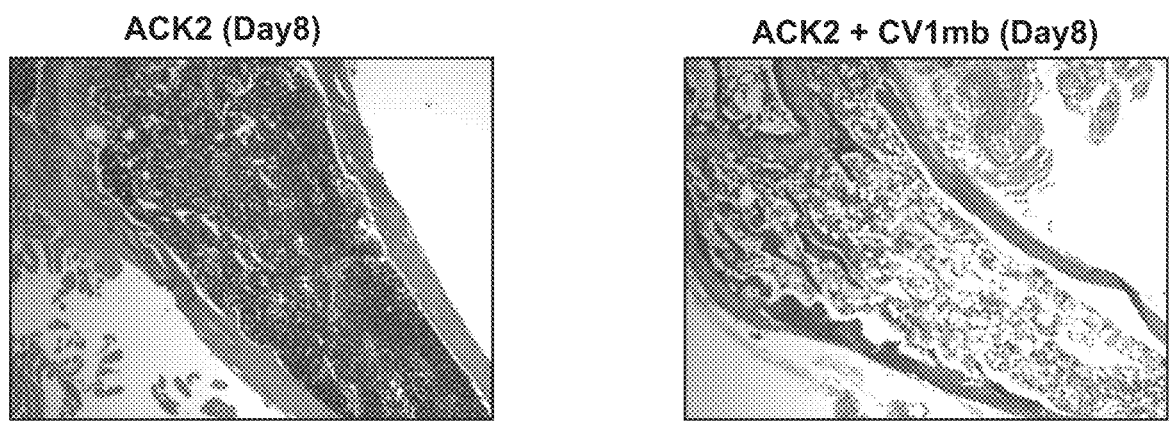

FIG. 15, Quantification of total number of long term hematopoietic stem cells (HSCs) based on FACS analysis. Wild-type mice were treated with either 500 μg of anti-CD117 antibody ACK2, CD47 antagonist CV1 (500 μg administered daily) as well as a combination of the two. Complete depletion of HSCs is observed in the ACK2+CV1 treated mice. B. Functional depletion of HSCs is observed in mice treated with ACK2+CV1 but mice treated with ACK2 alone retain transplantable HSCs. In order to demonstrate this depletion, whole bone marrow from treated mice was transplanted into lethally irradiated recipients. Support bone marrow was given to rescue recipients.

FIG. 16, A. CBC analysis of mice post 8 days of treatment with ACK2 (single IV dose of 500 UG), CV1mb (500 μg injected IP daily), and ACK2+CV1mb as compared to untreated controls. Combination of ACK2 and CV1mb led to a severe loss of hematocrit, hemoglobin and red blood cells. Slight loss of WBC was also observed. B Quantification of FACS analysis depicting depletion of phenotypic HSCs, as well as myeloid progenitors (CMP—common myeloid progenitor, GMP—granulocyte macrophage progenitor, MEP—megakaryote erythoid progenitor) 9 days post combination treatment. C. Functional depletion of HSCs is observed in mice treated with ACK2+CV1mb but mice treated with ACK2 alone retain transplantable HSCs. In order to demonstrate this depletion, whole bone marrow from treated mice was transplanted into lethally irradiated recipients. Support bone marrow was given to rescue recipients. D. H&E staining of a cross section of the femur depicting extensive loss of bone marrow cellularity in ACK2+CV1mb treated mice 8 days post treatment as compared to ACK2 alone.

FIG. 17, A. Quantification of granulocyte chimerism assessed by FACS analysis. ~70% granulocyte chimerism was observed 3-4 week after Lin– bone marrow cells were transplanted into ACK2+CV1mb treated mice. Three consecutive Lin– bone marrow transplants were given 6 days post ACK2 treatment. Chimerism was minimal in mice treated with ACK2 alone. B. B cell chimerism was observed in mice treated with ACK2+CV1mb, by FACS analysis of peripheral blood.

Each publication cited in this specification is hereby incorporated by reference in its entirety for all purposes.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

What is claimed is:

1. A method of hematopoietic stem cell engraftment in a mammal, the method comprising:
    contacting said mammal concomitantly with (i) a monoclonal antibody specific for CD117 at a dose of from 50 µg/kg body weight to 50 mg/kg body weight; and (ii) an agent that blocks interaction between CD47 and SIRPα, wherein the agent is selected from an anti-CD47 antibody, an anti-SIRPα antibody, a soluble SIRPα polypeptide or a fusion protein comprising a SIRPα polypeptide at a dose of from 50 µg/kg body weight to 100 mg/kg body weight; wherein the combination of doses is effective in ablating hematopoietic stem cells from bone marrow of said mammal; and
    introducing exogenous hematopoietic stem cells to said mammal, wherein the exogenous hematopoietic stem cells engraft to provide for long-term multilineage hematopoietic engraftment.

2. The method of claim 1, wherein the monoclonal antibody specific for CD117 is administered at a dose from 500 µg/kg body weight to 25 mg/kg body weight.

3. The method of claim 2, wherein the monoclonal antibody specific for CD117 is administered at a dose from 500 µg/kg mg/kg body weight to 10 mg/kg body weight.

4. The method of claim 3, wherein the monoclonal antibody specific for CD117 is administered at a dose from 500 µg/kg mg/kg body weight to 5 mg/kg body weight.

5. The method of claim 1, wherein the agent that blocks interaction between CD47 and SIRPα is administered at a dose from 5 mg/kg body weight to 50 mg/kg body weight.

6. The method of claim 5, wherein the monoclonal antibody specific for CD117 is administered at a dose from 10 mg/kg mg/kg body weight to 50 mg/kg body weight.

7. The method of claim 1 wherein the agent that blocks interaction between CD47 and SIRPα comprises a soluble SIRPα polypeptide.

8. The method of claim 7, wherein the soluble SIRPα polypeptide is a high affinity SIRPα variant.

9. The method of claim 8, wherein the soluble SIRPα polypeptide is CV1.

10. The method of claim 1 wherein the agent that blocks interaction between CD47 and SIRPα is an anti-CD47 antibody.

11. The method of claim 1, wherein the agent that blocks interaction between CD47 and SIRPα is an anti-SIRPα antibody.

12. The method according to claim 1, wherein said mammal is a human.

13. The method of claim 1, wherein the engraftment is performed in the absence of myeloablative conditioning.

14. The method of claim 1, wherein the mammal is immunocompetent.

15. The method according to claim 1, wherein said exogenous stem cells are allogeneic stem cells.

16. The method of claim 1, wherein the exogenous stem cells are autologous.

17. The method of claim 1, wherein said contacting is repeated at least twice.

* * * * *